United States Patent
Hart et al.

(10) Patent No.: US 10,285,589 B2
(45) Date of Patent: May 14, 2019

(54) FUNDUS IMAGE CAPTURE SYSTEM

(71) Applicant: Welch Allyn, Inc., Skaneateles Falls, NY (US)

(72) Inventors: Allen R. Hart, Knoxville, TN (US); Ynjiun P. Wang, Cupertino, CA (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 88 days.

(21) Appl. No.: 15/281,817

(22) Filed: Sep. 30, 2016

(65) Prior Publication Data

US 2018/0092530 A1 Apr. 5, 2018

(51) Int. Cl.
| | |
|---|---|
| *A61B 3/14* | (2006.01) |
| *A61B 3/15* | (2006.01) |
| *A61B 3/00* | (2006.01) |
| *A61B 3/12* | (2006.01) |

(52) U.S. Cl.
CPC ............ *A61B 3/152* (2013.01); *A61B 3/0025* (2013.01); *A61B 3/0058* (2013.01); *A61B 3/0075* (2013.01); *A61B 3/12* (2013.01)

(58) Field of Classification Search
CPC .. H04N 5/232; H04N 5/2251; H04N 5/23293; H04N 7/18; H04N 7/185; G02B 27/40; G02B 27/01; G02B 27/017; G02B 27/0172; G02B 27/0927; G02B 27/0093; G02B 27/0994; G02B 27/0961; G06F 3/01; G06F 3/013; G03B 21/28; G03B 3/00; G06T 5/004; G01B 11/24; A61B 3/013; A61B 3/0022; A61B 3/0025; A61B 3/005; A61B 3/085; A61B 3/0058; A61B 3/0075; A61B 3/0066; A61B 3/0091; A61B 3/10–3/14; A61B 3/15; A61B 3/102; A61B 3/107; A61B 3/113; A61B 3/145; A61B 3/152; A61B 3/156; A61B 3/158; A61B 3/1005; A61B 3/1015;
(Continued)

(56) References Cited

U.S. PATENT DOCUMENTS

| | | | |
|---|---|---|---|
| 4,953,969 A * | 9/1990 | Fedorov | A61F 9/008 351/221 |
| 5,784,148 A | 7/1998 | Heacock | |
| 6,000,799 A | 12/1999 | Van De Velde | |

(Continued)

FOREIGN PATENT DOCUMENTS

| | | |
|---|---|---|
| CN | 102626304 A | 8/2012 |
| CN | 205006859 U | 2/2016 |

(Continued)

OTHER PUBLICATIONS

Carrasco-Zevallos, O. et al., "Pupil Tracking Optical Coherence Tomography for Precise Control of Pupil Entry Position," Biomedical Optics Express; 6(9): 3405-3419, Sep. 1, 2015, 15 pages.
(Continued)

*Primary Examiner* — Mustak Choudhury
(74) *Attorney, Agent, or Firm* — Merchant & Gould P.C.

(57) ABSTRACT

A fundus image capture system operates to determine if the system has captured an image that identifies the fundus, a region of interest in the image, or the current field of view. According to the determination, the system can guide the user to operate the system to capture a desired fundus image.

16 Claims, 16 Drawing Sheets

(58) Field of Classification Search
CPC ... A61B 3/1025; A61B 3/1208; A61B 3/1225; A61B 3/1241
USPC ........ 351/200–215, 221, 222, 246; 345/7, 8, 345/157; 353/20, 98, 101, 121; 382/103, 382/107, 116, 117, 128, 131, 275
See application file for complete search history.

(56) References Cited

U.S. PATENT DOCUMENTS

| | | |
|---|---|---|
| 6,307,526 B1 | 10/2001 | Mann |
| 6,309,070 B1 | 10/2001 | Svetliza et al. |
| 6,325,511 B1 | 12/2001 | Mizouchi |
| 6,350,031 B1 | 3/2002 | Lashkari |
| 6,556,853 B1 | 4/2003 | Cabib et al. |
| 7,264,355 B2 | 9/2007 | Rathjen |
| 7,284,859 B2 | 10/2007 | Ferguson |
| 7,311,400 B2 | 12/2007 | Wakil et al. |
| 7,364,297 B2 | 4/2008 | Goldfain et al. |
| 7,380,938 B2 | 6/2008 | Chmielewski, Jr. et al. |
| 7,387,384 B2 | 6/2008 | Heine et al. |
| 7,488,294 B2 | 2/2009 | Torch |
| 7,621,636 B2 | 11/2009 | Su et al. |
| 7,784,940 B2 | 8/2010 | Goldfain et al. |
| 7,809,160 B2 | 10/2010 | Vertegaal et al. |
| 7,871,164 B2 | 1/2011 | Luther et al. |
| 7,926,945 B2 | 4/2011 | Dick et al. |
| 7,976,162 B2 | 7/2011 | Flitcroft |
| 8,347,106 B2 | 1/2013 | Tsuria et al. |
| 8,534,837 B2 | 9/2013 | Sayeram et al. |
| 8,620,048 B2 | 12/2013 | Nakano et al. |
| 9,211,064 B2 | 12/2015 | Wang |
| 9,237,847 B2 | 1/2016 | Wang et al. |
| 2002/0101568 A1 | 8/2002 | Eberl et al. |
| 2003/0208125 A1 | 11/2003 | Watkins |
| 2004/0254477 A1* | 12/2004 | Sekiguchi ............... A61B 3/14 600/476 |
| 2005/0043588 A1 | 2/2005 | Tsai |
| 2005/0110949 A1 | 5/2005 | Goldfain et al. |
| 2005/0254008 A1 | 11/2005 | Ferguson et al. |
| 2006/0147095 A1 | 7/2006 | Usher et al. |
| 2006/0268231 A1 | 11/2006 | Gil et al. |
| 2007/0174152 A1 | 7/2007 | Bjornberg et al. |
| 2008/0231803 A1 | 9/2008 | Feldon et al. |
| 2009/0225277 A1 | 9/2009 | Gil |
| 2009/0275929 A1 | 11/2009 | Zickler |
| 2009/0316115 A1 | 12/2009 | Itoh et al. |
| 2010/0014052 A1 | 1/2010 | Koschmieder et al. |
| 2010/0085538 A1 | 4/2010 | Masaki et al. |
| 2011/0001927 A1 | 1/2011 | Kasper |
| 2011/0043756 A1 | 2/2011 | Kahn et al. |
| 2011/0169935 A1 | 7/2011 | Henriksen |
| 2011/0234977 A1 | 9/2011 | Verdooner |
| 2011/0242306 A1 | 10/2011 | Bressler et al. |
| 2011/0299036 A1 | 12/2011 | Goldenholz |
| 2012/0050677 A1 | 3/2012 | Ohban |
| 2012/0121158 A1 | 5/2012 | Sekine et al. |
| 2012/0147327 A1 | 6/2012 | Shikaumi et al. |
| 2012/0169995 A1 | 7/2012 | Mohr et al. |
| 2012/0200690 A1 | 8/2012 | Beasley |
| 2012/0218301 A1 | 8/2012 | Miller |
| 2012/0229617 A1 | 9/2012 | Yates et al. |
| 2012/0248196 A1 | 10/2012 | Wang |
| 2012/0249956 A1 | 10/2012 | Narasimha-Iyer et al. |
| 2012/0257163 A1 | 10/2012 | Dyer et al. |
| 2012/0320340 A1 | 12/2012 | Coleman, III |
| 2013/0010260 A1 | 1/2013 | Tumlinson et al. |
| 2013/0016320 A1 | 1/2013 | Naba |
| 2013/0057828 A1 | 3/2013 | de Smet |
| 2013/0063698 A1* | 3/2013 | Akiba ..................... A61B 3/12 351/206 |
| 2013/0169934 A1 | 7/2013 | Verdooner |
| 2013/0176533 A1 | 7/2013 | Raffle et al. |
| 2013/0194548 A1 | 8/2013 | Francis et al. |
| 2013/0208241 A1 | 8/2013 | Lawson et al. |
| 2013/0222763 A1 | 8/2013 | Bublitz et al. |
| 2013/0229622 A1 | 9/2013 | Murase et al. |
| 2013/0234930 A1 | 9/2013 | Palacios Goerger |
| 2013/0250242 A1 | 9/2013 | Cheng et al. |
| 2014/0022270 A1 | 1/2014 | Rice-Jones |
| 2014/0028976 A1* | 1/2014 | Tanassi ................ A61B 3/152 351/208 |
| 2014/0104573 A1 | 4/2014 | Iwanaga |
| 2014/0192320 A1 | 7/2014 | Tsao |
| 2014/0204340 A1 | 7/2014 | Verdooner |
| 2015/0223686 A1 | 8/2015 | Wang |
| 2016/0249804 A1 | 9/2016 | Wang |

FOREIGN PATENT DOCUMENTS

| | | |
|---|---|---|
| CN | 105433899 A | 3/2016 |
| CN | 205181314 U | 4/2016 |
| EP | 2689719 A1 | 1/2014 |
| JP | 3569026 B2 | 9/2004 |
| JP | 2013-059551 A | 4/2013 |
| KR | 102013001079 A | 1/2013 |
| WO | 2004089214 A2 | 10/2004 |
| WO | 2008106802 A1 | 9/2008 |
| WO | 2010080576 A1 | 7/2010 |
| WO | 2012009702 A1 | 1/2012 |
| WO | 2012134272 A1 | 10/2012 |
| WO | 2013041658 A1 | 3/2013 |
| WO | 2013107464 A1 | 7/2013 |

OTHER PUBLICATIONS

Moscaritolo, Michael et al., "A Machine Vision Method for Automated Alignment of Fundus Imaging Systems," Ophthalmic Surgery Lasers & Imaging; 41(6): 607-613, Sep. 29, 2010, 7 pages.

Sahin, B. et al., "Adaptive Optics With Pupil Tracking for High Resolution Retinal Imaging," Biomedical Optics Express; 3(2): 225-239, Feb. 1, 2012, 15 pages.

Hammer, Daniel X. et al., Adaptive Optics Scanning Laser Ophthalmoscope for Stabilized Retinal Imaging, Optics Express; 14(8): 3354-3367, Apr. 17, 2006, 14 pages.

Markow, Michael S. et al., "Real-Time Algorithm for Retinal Tracking," IEEE Transactions on Biomedical Engineering; 40(12): 1269-1281, Dec. 1993, 13 pages.

Sheehy, Christy K. et al., "High-speed, Image-based eye tracking with a scanning laser ophthalmoscope," Biomedical Optics Express; 3(10): 2611-2622, Oct. 1, 2012, 12 pages.

International Search Report and Written Opinion in PCT/US2016/015653, dated May 3, 2016, 11 pages.

"A Portable, Scalable Retinal Imaging System," TI Engibous Competition Report (Spring 2012), Rice University, http://www.ti.com/corp/docs/university/docs/Rice_University_mobileVision%20Final%20Report.pdf (96 pages).

Girdwain, "Goggles Differentiate Between Stroke and Vertigo," Today's Geriatric Medicine, vol. 6 No. 4 p. 8, Today's GeriatricMedicine, Oct. 1, 2013, 2 pages.

Johns Hopkins Medicine, "Small Johns Hopkins-led study finds portable device diagnoses stroke with 100 percent accuracy," www.hopkinsmedicine.org/se/util/display_mod.cfm?MODULE=/se-server/mod/modules/semod_printpage/mod_default.cfm&PageURL-/news/media/releases/is_i . . . , Mar. 5, 2013, 2 pages.

International Search Report and Written Opinion in PCT/US2015/015124 dated May 15, 2015, 10 pages.

Brown et al., "Comparison of image-assisted versus traditional fundus examination," Eye and Brain, Dovepress, Feb. 2013, vol. 5, pp. 1-8.

Muller et al., "Non-Mydriatic Confocal Retinal Imaging Using a Digital Light Projector," Ophthalmic Technologies XXIII, 2013, downloaded from: http://proceedings.spiedigitallibrary.org, 8 pages.

Paques et al., "Panretinal, High-Resolution Color Photography of the Mouse Fundus," Investigative Ophthalmology & Visual Science, Jun. 2007, vol. 48, No. 6, pp. 2769-2774.

VISUCAMPRO NM—The Non-Mydriatic Fundus Camera System from Carl Zeiss, Carl Zeiss Meditec, International, 2005, 1 page.

(56) References Cited

OTHER PUBLICATIONS

Search Report from European Patent Appl. No. 17 19 3866.5 dated Mar. 9, 2018, 8 pages.

* cited by examiner

FUNDUS IMAGE CAPTURE SYSTEM

BACKGROUND

An ophthalmoscope is device used to image the fundus of an eye (or eye fundus) and other structures of the eye. The eye fundus image shows the interior surface of the eye opposite the lens, including the retina, optic disc, macula and fovea, and posterior pole. This imaging is used to determine the health of the retina and vitreous humor and to evaluate conditions such as hypertension, diabetic retinopathy, and papilledema. The ophthalmoscope device may include a camera that is used to capture the images and a display used to display the images obtained by the ophthalmoscope device. Medical professionals use the images to diagnose and treat various diseases.

Typically, the ophthalmoscope is a hand-held device or a headband-mounted device that is worn by a user, such as a caregiver or medical professional. To properly capture fundus images, the eye must be first aligned properly with the device. The user then interacts with the device to trigger a capture of an image. For example, the user needs to press a button or select a control on a graphic user interface (GUI) on the device to capture the image. Misalignment between the device and the eye, or unwanted movement of the device against the eye, can cause mislocation of the eye fundus and produce a fundus image of inferior quality.

SUMMARY

In general terms, this disclosure is directed to a fundus image capture system. In one possible configuration and by non-limiting example, the system operates to identify a region of interest using a predetermined image mask. Various aspects are described in this disclosure, which include, but are not limited to, the following aspects.

One aspect is an apparatus for producing a fundus image. The apparatus includes a processor, an image capture device for capturing images, and a computer readable storage device storing software instructions that, when executed by the processor, cause the apparatus to: obtain an image from the image capture device; apply a mask to the image to generate a masked image; identify a predetermined contour in the masked image; calculate a centroid of the predetermined contour; and generate guide information usable to guide a user to operate the apparatus to capture an image showing a region of interest, the guide information generated based on the centroid of the predetermined contour.

Another aspect is a method of capturing an eye fundus image. The method includes obtaining an image from an image capture device; applying a mask to the image to generate a masked image; identifying a largest contour in the masked image; calculating a centroid of the largest contour; displaying the image on a display device; and displaying a target point on the display device, the target point being arranged at a location in the image corresponding to the centroid of the largest contour in the masked image.

Yet another aspect is a computer-readable storage medium comprising software instructions that, when executed by a processing device, cause the processing device to generate an image mask for identifying a region of interest in a digital image, wherein the image mask defines a center region and a plurality of longitudinal regions, the center region and the longitudinal regions configured to selectively filter corresponding regions of the digital image, the longitudinal regions extending from the center region and being spaced apart from each other with predetermined gaps.

DETAILED DESCRIPTION

Figure 1:
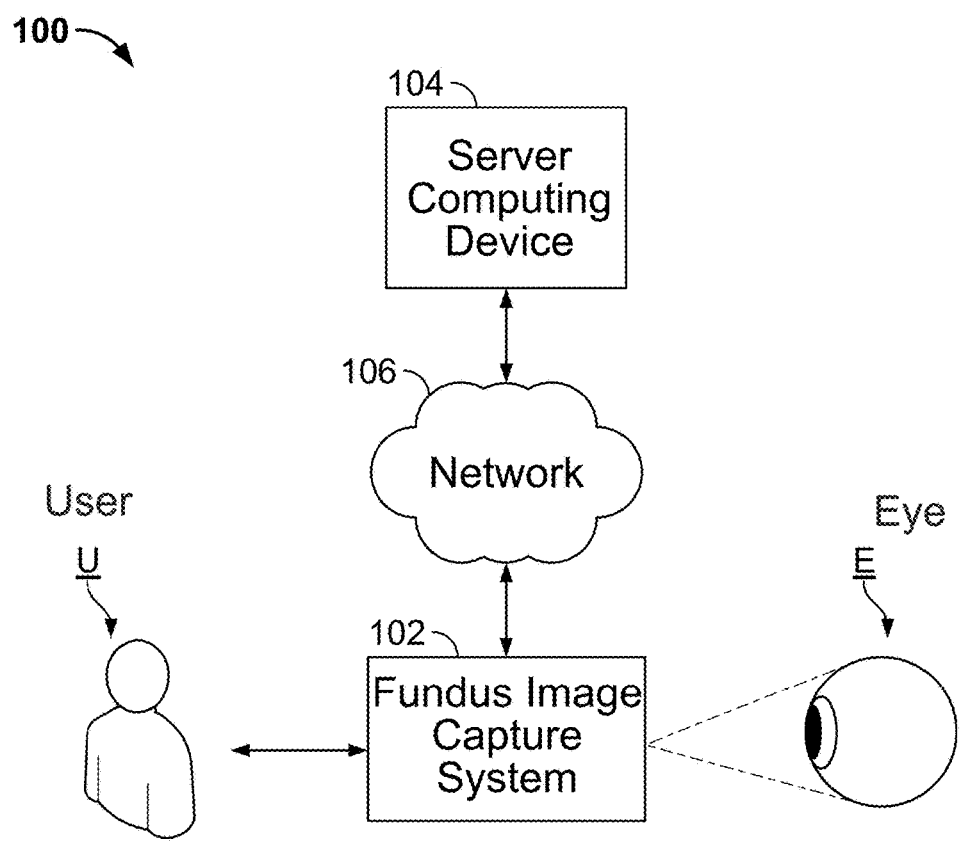
FIG. 1 is a schematic diagram of an example system for producing an eye fundus image.

Various embodiments will be described in detail with reference to the drawings, wherein like reference numerals represent like parts and assemblies throughout the several views.

FIG. 1 is a schematic diagram of an example system 100 for capturing a fundus image of an eye E. In this example, the system 100 includes a fundus image capture system 102, a server computing device 104, and a network 106.

The fundus image capture system 102 is used to assist the user U in screening for, monitoring, and/or diagnosing various eye diseases or other diseases. As described herein, the fundus image capture system 102 is configured to capture one or more fundus images of the eye E of a subject, such as a patient. As used herein, "fundus" refers to the eye fundus including the retina, optic disc, macula and fovea, posterior pole, and other elements. The fundus image is reviewed by a user U for various purposes. For example, the fundus image can be used to screen the subject for eye diseases, or to diagnose or monitor the progression of various diseases. It will be appreciated that the user that operates the fundus image capture system 102 can be different from the user U evaluating the resulting fundus image.

The user can be a caregiver and medical professional who are experienced in operating the fundus image capture system. The user can also be any person (including the subject him- or herself) who are not familiar with the fundus image capture system. Capturing a fundus image is not easy for such users without enough experience of using the fundus image capture system, because it is difficult to handle the system to arrange it against the pupil in the accurate position and orientation. For example, when a user uses a handheld fundus image capture device (e.g., ophthalmoscope), it is difficult to keep track of the center of pupil. In particular, when entering the fundus, the user may get lost due to a slight deviation (such as a few millimeters) off from the pupil center. This situation becomes worse when the subject has a small pupil size. In addition, the user may also unintentionally tile the device, resulting in the optical center misaligned with the pupil optical center. This causes losing the field of view of fundus. As described herein, the fundus image capture system 102 is configured to allow unskilled users to easily track a region of interest in the eye and capture a fundus image.

In some examples, at least a portion of the fundus image capture system 102 is configured to be held by the hand of the user U. In other examples, the fundus image capture system 102 is configured to be worn by the subject to capture the fundus image of the subject. An example configuration of the fundus image capture system 102 is described in more detail with reference to FIG. 2.

In some embodiments, the system 100 can include the server computing device 104 that is in data communication with the fundus image capture system 102 via the network 106. The server computing device 104 is configured to receive data from the fundus image capture system 102 and perform additional processing and/or storage in an electronic medical record (EMR). In some examples, the fundus image capture system 102 is configured to send data associated with the images captured and/or processed therein to the server computing device 104, which then processes and store the data for various purposes.

The fundus image capture system 102 and the server computing device 104 communicate through the network 106. In one example, the fundus image capture system 102 and network 106 are part of a CONNEX™ system from Welch Allyn of Skaneateles Falls, N.Y., although other systems can be used.

In another example, the server computing device 104 can be a distributed network, commonly referred to as a "cloud" server. The fundus image capture system 102 communicates with the cloud server through non-proprietary, industry standard messaging. Data encryption is also based on industry standards.

The network 106 is an electronic communication network that facilitates communication between the fundus image capture system 102 and the server computing device 104. An electronic communication network is a set of computing devices and links between the computing devices. The computing devices in the network use the links to enable communication among the computing devices in the network. The network 106 can include routers, switches, mobile access points, bridges, hubs, intrusion detection devices, storage devices, standalone server devices, blade server devices, sensors, desktop computers, firewall devices, laptop computers, handheld computers, mobile telephones, and other types of computing devices.

In various embodiments, the network 106 includes various types of links. For example, the network 106 can include wired and/or wireless links, including Bluetooth, ultra-wideband (UWB), 802.11, ZigBee, and other types of wireless links. Furthermore, in various embodiments, the network 106 is implemented at various scales. For example, the network 106 can be implemented as one or more local area networks (LANs), metropolitan area networks, subnets, wide area networks (such as the Internet), or can be implemented at another scale. Additionally, the network 106 includes networks formed between the fundus image capture system 102 and a peripheral device using a wireless network protocol (e.g., a mouse connected using Bluetooth, etc.).

Figure 2:
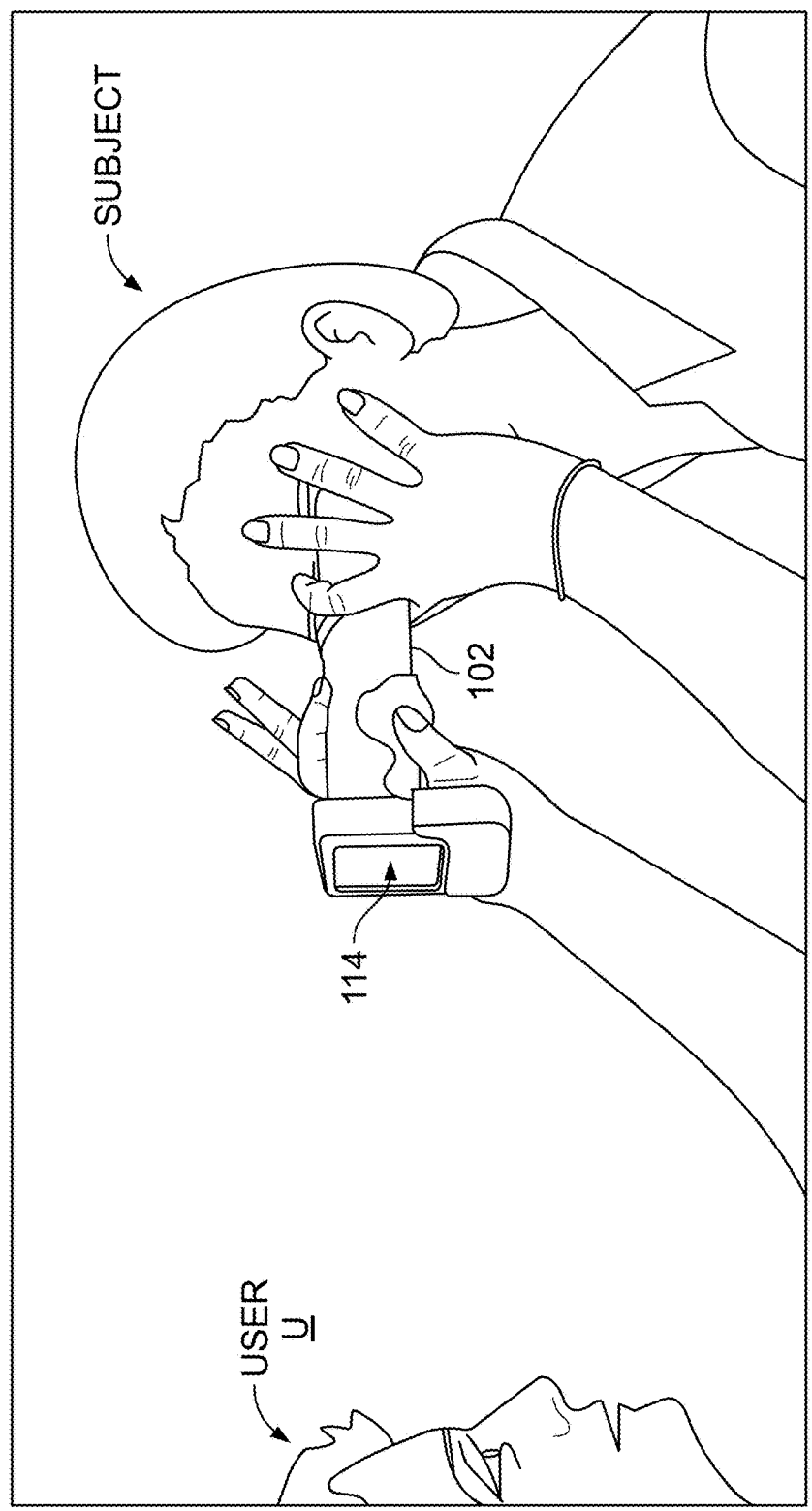
FIG. 2 illustrates an example fundus image capture system in use on the subject.

FIG. 2 illustrates an example of the fundus image capture system 102 in use on the subject. In the illustrated example, the fundus image capture system 102 is an apparatus configured as an independent handheld device such that the user places the fundus image capture system 102 against the subject's face with an end adjacent to or touching the subject's face surrounding the desired eye socket. In this document, therefore, the fundus image capture system 102 is also referred to as the fundus image capture apparatus or device 102.

The fundus image capture system 102 includes a physical structure configured to house and hold various components of the fundus image capture system 102. Such a physical structure can incorporate at least one of an image capture device, an image process device, and a display device, which are further described in FIG. 3.

In some embodiments, the physical structure of the fundus image capture system 102 is configured to be held by the user U for viewing and capturing images of the fundus. For example, the fundus image capture system 102 can be used with PanOptic™ Ophthalmoscope or iExaminer™ from Welch Allyn of Skaneateles Falls, N.Y.

In other examples, the fundus image capture system 102 includes a mobile computing device and an attachment device configured to mount the mobile computing device. For example, a user can attach the attachment device to an existing mobile computing device, and then take an image of the patient while monitoring a screen of the mobile computing device. The attachment device can be configured to be conveniently held by a user so that the user support the attachment device at a predetermined position close to the subject and capture an image as desired. For example, the system 102 can be used with PanOptic™ Ophthalmoscope or iExaminer™ from Welch Allyn of Skaneateles Falls, N.Y. Other examples of the system 102 can employ at least part of the disclosure in U.S. patent application Ser. No. 14/633,601, titled THROUGH FOCUS RETINAL IMAGE CAPTURING, filed Feb. 27, 2015, the disclosure of which is incorporated herein by reference in its entirety. Another example fundus image capture system 102 is configured similarly to a device disclosed in U.S. patent application Ser. No. 14/557,146, titled DIGITAL COLPOSCOPE SYSTEM, filed Dec. 1, 2014, the entirety of which is incorporated herein by reference.

In yet other examples, the physical structure of the system 102 includes a support structure configured to couple to a subject. For example, the support structure is an eye glasses frame or a headband. An example of the physical structure of this type is disclosed in U.S. patent application Ser. No.

14/177,594, titled OPHTHALMOSCOPE DEVICE, filed Feb. 11, 2014, the disclosure of which is incorporated herein by reference in its entirety.

Yet other embodiments of the physical structure are also possible. In some examples, the physical structure of the fundus image capture system 102 includes all mechanical and electrical structures, and hardware and software as a single unit. In other examples, the fundus image capture system 102 is a digital ophthalmoscope that wirelessly transfers images to a computing device (e.g., mobile computing device or server) for processing. Other various examples are also possible.

Figures 3, 4:
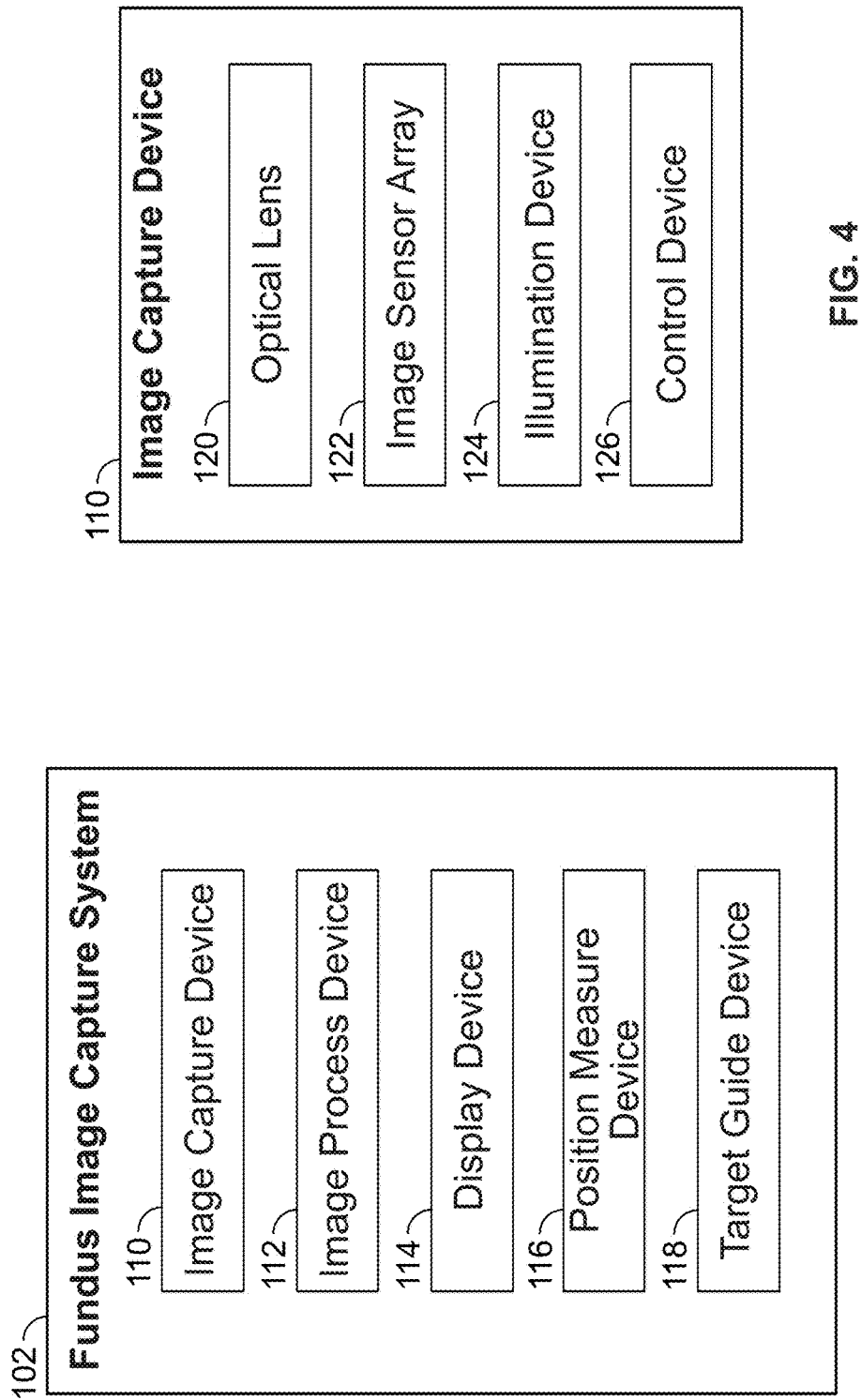
FIG. 3 illustrates an example of the fundus image capture system of FIG. 2.
FIG. 4 illustrates an example image capture device.

FIG. 3 illustrates an example of the fundus image capture system 102. In this example, the fundus image capture system 102 includes an image capture device 110, an image process device 112, a display device 114, a position measure device 116, and a target guide device 118.

The image capture device 110 is a device configured to capture images of the subject, such as the eye E of the subject. In some examples, the image capture device 110 capture images continuously (e.g., video recording or burst shots) as the system 102 moves, and some or all of the captured images (also referred to herein as image frames) are processed and evaluated as described herein. In some examples, the methods described herein are applied to the captured images one-by-one until a desired fundus image is determined to have been obtained. Since the methods are performed for each image in a very short period of time (e.g., 30 milliseconds), a plurality of captured images appears to be processed in real-time.

In some examples, the image capture device 110 includes a camera configured to capture reflection (e.g., infrared reflection) from an object to be imaged. An example of the image capture device 110 is illustrated and described in more detail with reference to FIG. 4.

The image process device 112 is a device configured to retrieve one or more images (also referred to herein as image frames) from the image capture device 110 and process the images to obtain a fundus image as desired. As described herein, the image process device 112 operates to perform image processing to determine that a particular image shows a fundus image of the subject as desired. An example of the image process device 112 is illustrated and described in more detail with reference to FIG. 5.

The display device 114 is a device configured to display one or more images (e.g., one or more fundus images) in original and/or processed formats so that the user reviews the images for diagnosis or monitoring. In some examples, the display device 114 is configured as a touch sensitive display screen and can further present a user interface for enabling the user to interact with the system 102. For example, the user interface includes graphical control widgets displayed on the display device 114. As described herein, the user interface can include one or more target guide marks (such as a target point and a track point described herein) that represent the arrangement (such as position and/or orientation) of the apparatus 102 relative to a region of interest in the subject's eye.

In some examples, the display device 114 is a display of a computing device, such as the screen of a mobile computing device (e.g., smartphones, tablets computers, and other mobile devices).

The position measure device 116 operates to detect the position and orientation of the fundus image capture system 102. In some examples, the position measure device 116 is configured to track the position of the image capture device 110 (e.g., a camera thereof) and the optical axis orientation.

With the fundus tracking information generated as described herein, the position measure device 116 can provide smooth user feedback to guide a user to move the fundus image capture system 102 such that the camera optical axis points to the subject's eye (or fundus).

In some examples, the position measure device 116 includes one or more sensors for determining position and orientation. Examples of such sensors include a gyroscope, which measures changes in orientation and/or changes in rotational velocity, an accelerometer, which measures accelerations to determine changes in velocity and/or changes in position, and a magnetometer, which measures magnetic fields to determine absolute orientation. Other types of sensors can also be used in other examples.

The target guide device 118 operates to provide information for guiding the user to operate the apparatus 102 to capture a desired image of the subject's eye. In some examples, the target guide device 118 generates target guide marks or icons, and other information of various types (such as visual, audible, and tactile).

In some examples, the target guide device 118 displays visual marks, such as the target point and the track point (as described below) on the display device 114 as the fundus image capture system 102 moves. Such visual marks indicate whether the fundus image capture system 102 is arranged to capture a desired fundus image. The target guide device 118 is described in more detail with reference to FIGS. 11-15.

In some embodiments, the image capture device 110, the image process device 112, the display device 114, and the position measure device 116 are implemented in a single computing device. In other embodiments, at least one of the image capture device 110, the image process device 112, the display device 114, and the position measure device 116 is implemented in different computing devices.

FIG. 4 illustrates an example of the image capture device 110. In this example, the image capture device 110 includes an optical lens element 120, an image sensor array 122, an illumination device 124, and a control device 126.

The image capture device 110 is configured to capture images of the fundus of the subject. The image capture device 110 is in communication with the image process device 112. The images obtained by the image capture device 110 can be transmitted to the image process device 112 for subsequent processes.

In some embodiments, the images captured by the image capture device 110 are digital images. The digital images can be captured in various formats, such as JPEG, BITMAP, TIFF, etc. In other embodiments, the images captured by the image capture device 110 are film images. In yet other embodiments, the image capture device 110 includes a digital video camera. Yet other embodiments of the image capture device 110 are possible as well.

In some examples, the optical lens element 120 includes a variable focal lens, such as a lens moved by a step motor, or a fluid lens (also known as a liquid lens). Other embodiments of the optical lens element 120 are also possible.

The image sensor array 122 is a device configured to receive and process light reflected by the subject's fundus. The image sensor array 122 can be of various types. For example, the image sensor array 122 is a complementary metal-oxide semiconductor (CMOS) sensor array (also known as an active pixel sensor (APS)) or a charge coupled device (CCD) sensor. In some examples, the image sensor array can be configured to receive and process infrared reflection.

The example image sensor array 122 includes photodiodes that have a light-receiving surface and have substantially uniform length and width. During exposure, the photodiodes convert the incident light to a charge. The image sensor array 122 can be operated in various manners. In some embodiments, the image sensor array 122 is operated as a global reset, that is, substantially all of the photodiodes are exposed simultaneously and for substantially identical lengths of time. In other embodiments, the image sensor array 122 is used with a rolling shutter mechanism, in which exposures move as a wave from one side of an image to the other. Other mechanisms are also possible to operate the image sensor array 122 in yet other embodiments.

The illumination device 124 is a device configured to generate and direct light towards the eye of the subject when the image capture device 110 is in use so that the structures of the eye may be imaged. In some embodiments, the illumination device 124 includes one or more light emitting diodes, incandescent bulbs, or fiber optic cables. The illumination device 124 can also include infrared light sources, such as infrared LEDs. Yet other embodiments of the illumination device 124 are possible as well. In some embodiments, the illumination device 124 is configured to create multiple illumination conditions, each having a different intensity (i.e., brightness) of light. However, some embodiments of the image capture device 110 do not include an illumination device 124.

The control device 126 is a device configured to control the operation of the image capture device 110 to capture images. In some embodiments, the control device 126 is configured to control the optical lens element 120, the image sensor array 122, and the illumination device 124. In some embodiments, the control device 126 is in communication with the image process device 112.

Figure 5:
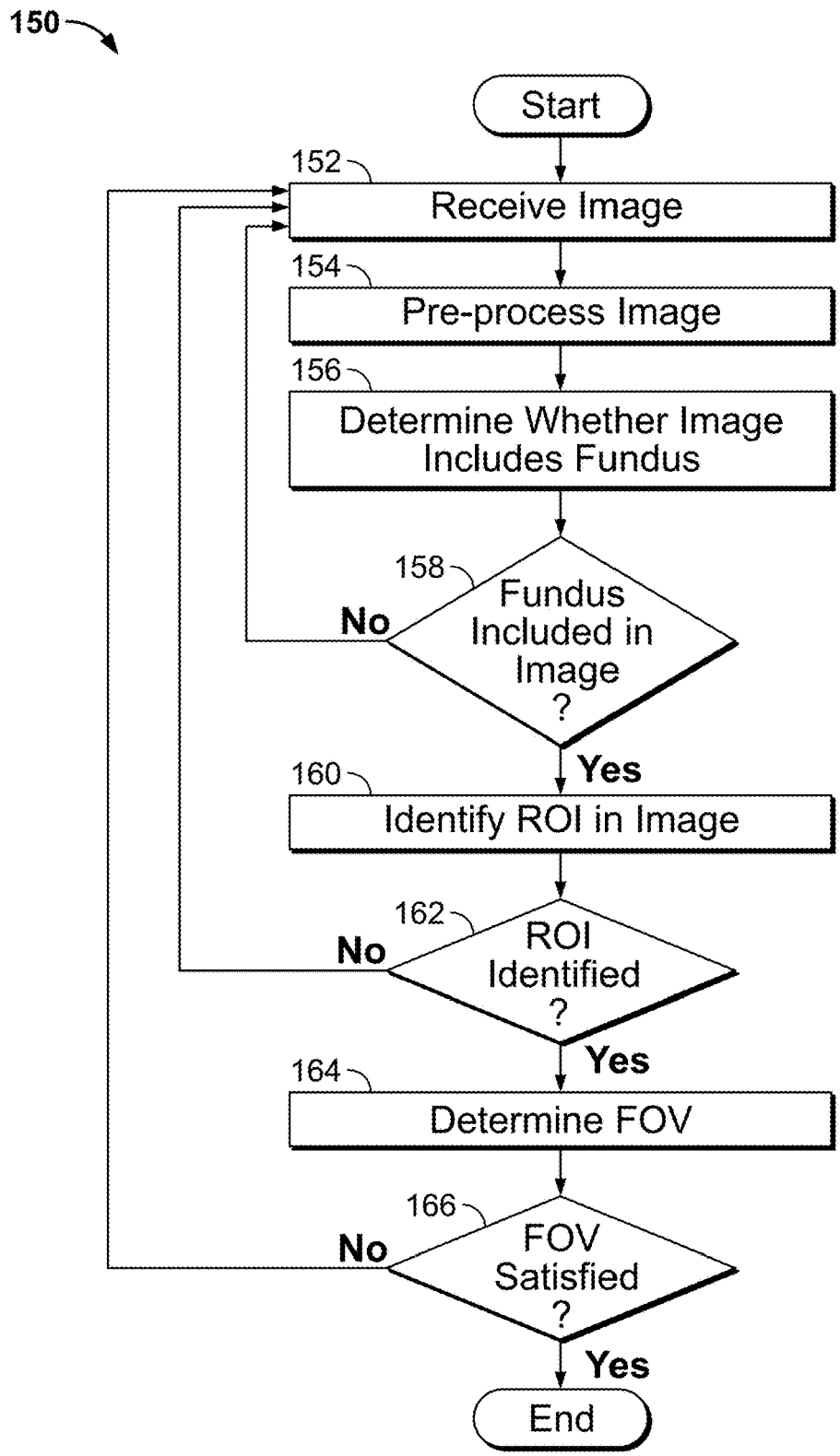
FIG. 5 is a flowchart of an example method for capturing a desired fundus image.

FIG. 5 is a flowchart of an example method 150 for capturing a desired fundus image, using the image process device 112. Although the method 150 is described to include operations 152, 154, 156, 158, 160, 162, 164, and 166, it is also possible in other examples that the method 150 includes only some of these operations, and/or additional operations associated with the operations described herein.

Figure 21:
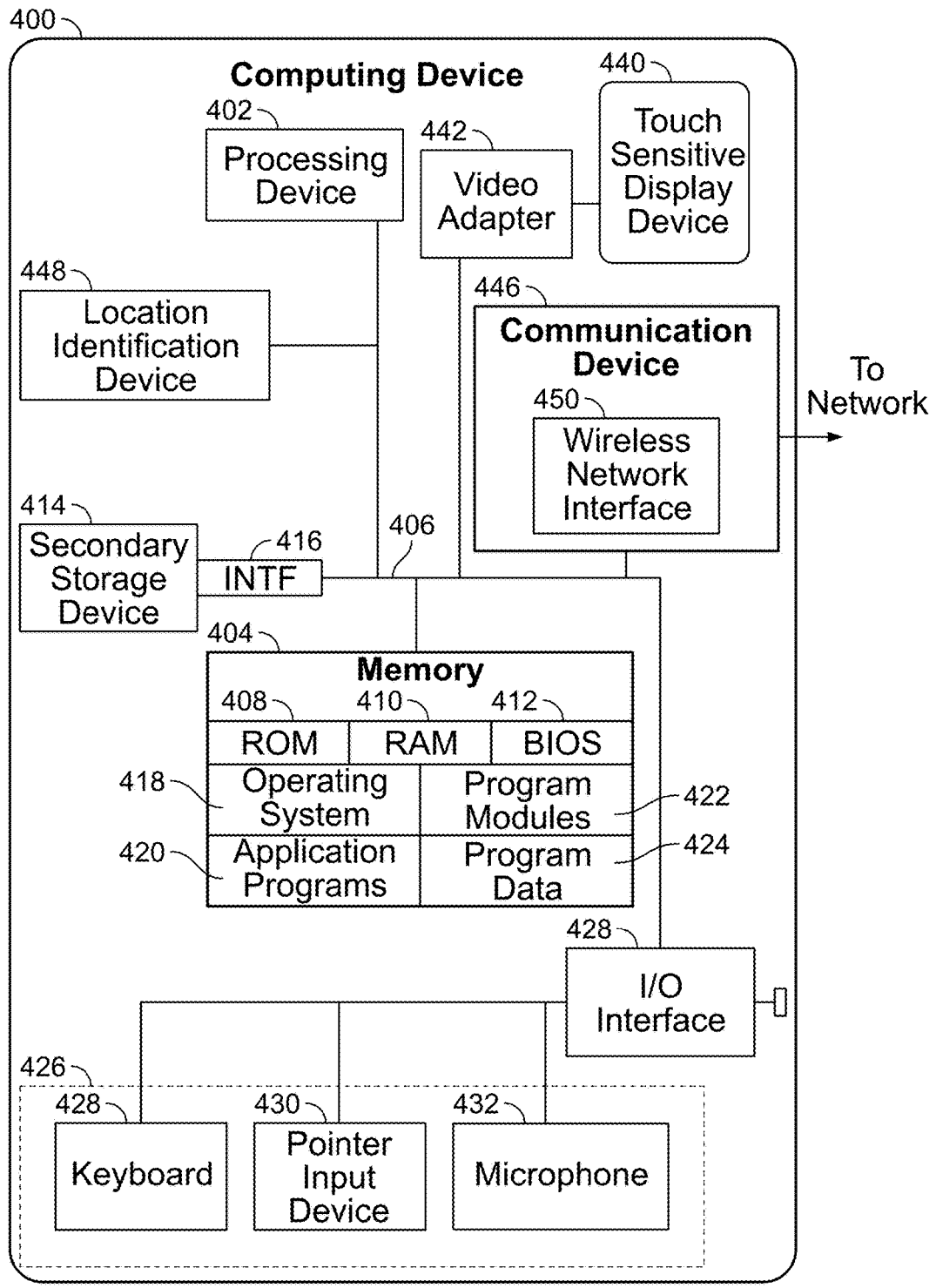
FIG. 21 illustrates an exemplary architecture of a computing device which can be used to implement aspects of the present disclosure.

In one implementation, the steps in the method 150 are implemented as a software application running on a computing device, as illustrated in FIG. 21. In some embodiments, the method 150 is developed with OpenCV library. Other libraries can also be used to implement the steps of the method 150.

The method 150 can begin at operation 152 in which the image process device 112 receives an image or image frame from the image capture device 110. As described herein, the image capture device 110 can continuously capture images while the apparatus 102 is moved by the user against the subject's face, eye, or fundus. The image process device 112 can receive one or more of the captures images from the image capture device 110 in real-time.

At operation 154, the image process device 112 performs a preliminary processing on the image. Various image processing can be performed to enhance fundus tracking.

In some examples, the image can be first converted to a gray scale image. A linear filter is then applied to the image using convolution. The linear filter can be configured to remove noise from the image and intensify the contrast of the image. This linear filter operates to improve fundus tracking by emphasizing edges in the image. For example, when an image is captured in a dark environment, the reflection (e.g., infrared reflection) is not bright enough to show edges in the image with sufficient emphasis to be counted. Further, when the image contains too much detail, the value of edge detection becomes diluted. The preliminary image processing operation improves the functionality of fundus tracking.

At operation 156, the image process device 112 determines whether the image at least partially includes a fundus. As the user moves the apparatus 102 against the subject's face, the image capture device 110 of the apparatus 102 can capture anything other than the fundus, such as other portions of the subject's face (e.g., the subject's cheek, forehead, eyebrow, or ear) or any background objects (e.g., desk, table, or wall). At this operation, the image process device 112 determines whether the captured image actually includes the subject's fundus, and identify whether the image incorrectly appears to include the subject's fundus (i.e., a false positive error). An example of the operation 154 is described in more detail with reference to FIG. 6.

At operation 158, if it is determined that the image includes a fundus ("YES" at this operation), the method 150 moves on to operation 160. Otherwise ("NO" at this operation), the method 150 returns to the operation 152 to receive a next image from the image capture device 110 and repeat the subsequent operations.

At operation 160, the image process device 112 operates to identify a region of interest (ROI) in the image. For example, once it is determined that the fundus is at least partially identified in the captured image (the operation 154), the image process device 112 further processes the image to locate a ROI in the fundus. An example of the operation 158 is described in more detail with reference to FIG. 8.

At operation 162, if it is determined that the ROI has been identified in the image ("YES" at this operation), the method 150 moves on to operation 164. Otherwise ("NO" at this operation), the method 150 returns to the operation 152 to receive a next image from the image capture device 110 and repeat the subsequent operations.

At operation 164, the image process device 112 operates to determine a field of view (FOV) in the captured image. The field of view can represent the user's current depth into the fundus. In some examples, the apparatus 102 determines whether the field of view is currently desirable and, if not, assists the user to move the apparatus 102 to achieve a desired field of view (e.g., a full field of view). An example of the operation 162 is described in more detail with reference to FIG. 16.

At operation 166, if it is determined that a desired field of view has been achieved in the image ("YES" at this operation), the method 150 continues any subsequent operations. Otherwise ("NO" at this operation), the method 150 returns to the operation 152 to receive a next image from the image capture device 110 and repeat the subsequent operations.

Figure 6:
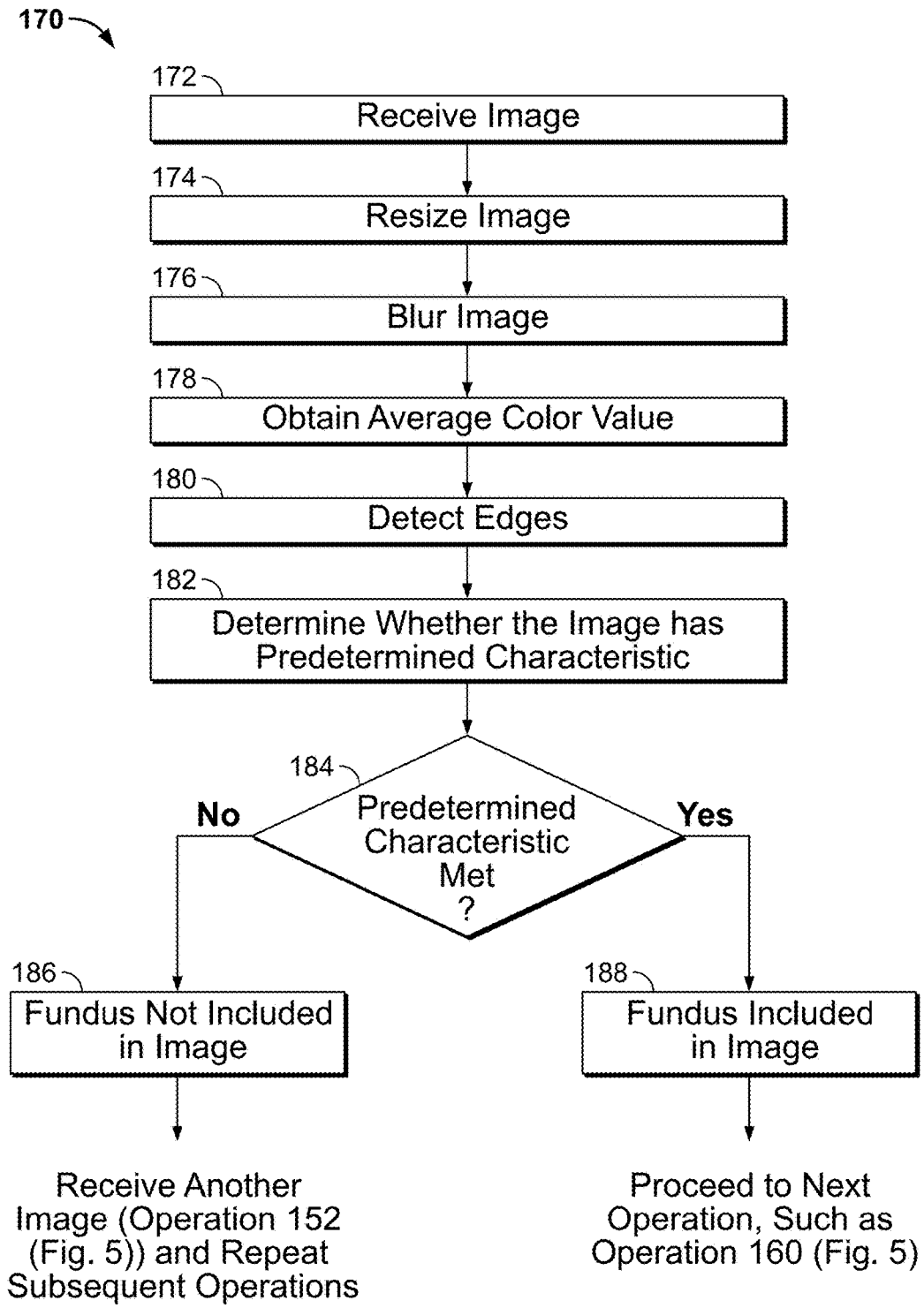
FIG. 6 is a flowchart of an example method for determining whether the captured image includes a fundus.

FIG. 6 is a flowchart of an example method 170 for determining whether the captured image includes a fundus. In some examples, the method 170 is performed by the image process device 112 to implement the operation 156 in FIG. 5. In the method 170, the image process device 112 determines if the fundus has been found as the user manipulates and moves the apparatus 102 against the subject's face or eye.

In one implementation, the steps in the method 170 are implemented as a software application running on a computing device, as illustrated in FIG. 21. In some embodiments, the method 170 is developed with OpenCV library. Other libraries can also be used to implement the steps of the method 170.

Although the method 170 is described to include the operations illustrated in FIG. 6, it is also possible in other examples that the method 170 includes only some of these operations, and/or additional operations associated with the operations described herein. For example, some of the illustrated operations are optional depending on the attributes (e.g., size or quality) of the captured image.

The method 170 begins at operation 172 in which the image process device 112 receives an image captured by the image capture device 110. As described herein, in some examples, the captured image can be pre-processed as described in FIG. 6 before the image is processed in the method 170.

At operation 174, the image process device 112 resizes the image. In some examples, the image is reduced to a smaller size to decrease the number of cycles needed to complete the subsequent processes, such as the subsequent operations in the method 170. For example, when the fully scale image has too much detail that are not interested, the fully scale image requires more computing resources for image processing than a smaller image. By way of example, the image can be resized to 1/0 scale.

At operation 176, the image process device 112 blurs the scaled image to remove details that are not interesting. This blurring process is used to prevent detection of irrelevant edges or minor edges and only to focus on hard edges, such as the bridge of a nose, the edge of eyelid, the edges of other facial elements, the edges of environmental objects around the subject's face, and other hard edges.

At operation 178, the image process device 112 obtains an average color value of the scaled image. The average color value of the scaled image can be calculated using various known algorithms.

At operation 180, the image process device 112 performs edge detection. In some examples, the image process device 112 calculates the amount of edges that are detected in the scaled image. For example, the amount of edges can be determined as the number of pixels constituting the edges. Other ways to measure the amount of edges are also possible in other examples.

Figure 7:
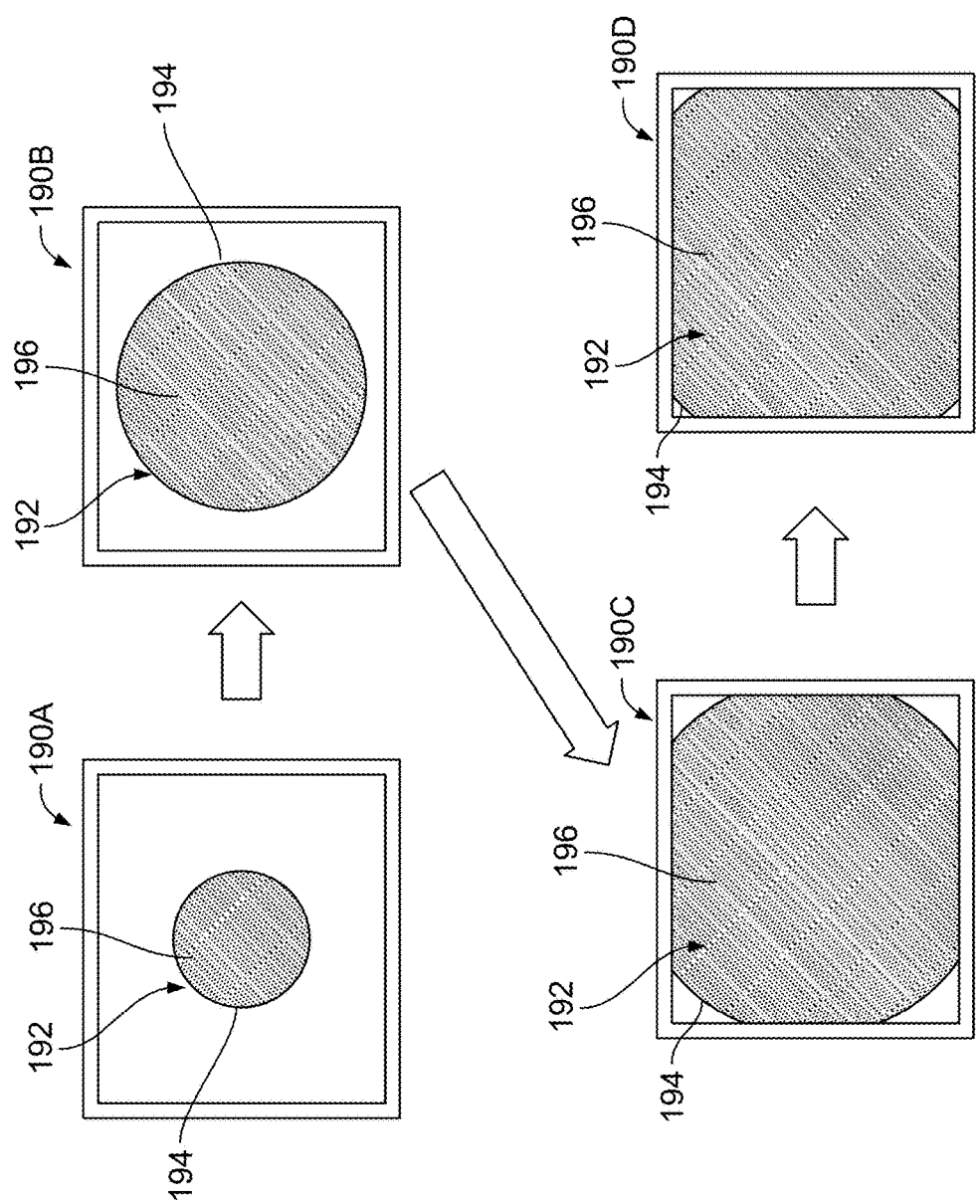
FIG. 7 schematically illustrates different images with different average color values and edge characteristics.

At operation 182, the image process device 112 determines whether the scaled image has a predetermined characteristic that is representative of a fundus in the scaled image. In some examples, the predetermined characteristic is associated with at least one of a color value and an edge characteristic, as illustrated in FIG. 7. For example, the image process device 112 can determine whether the average color value of the scale image, as obtained in the operation 178, meets a color threshold value that is indicative of an image including a fundus. In addition or alternatively, the image process device 112 determines whether the amount of edges (e.g., the number of pixels constituting the edges) in the scaled image, as obtained in the operation 180, meets an edge threshold value that is indicative of an image including a fundus.

At operation 184, if it is not determined that the scaled image has the predetermined characteristic ("NO" at this operation), the method 170 moves on to operation 186, in which the image process device 112 recognizes that the image does not show a fundus. As such, the image is not considered to include the fundus to be detected. Then, the image process device 112 can receive another image taken by the image capture device 110 (at the operation 152) and perform the subsequent operations as described herein.

Alternatively, if it is determined that the scaled image has the predetermined characteristic ("YES" at this operation), the method 170 goes to operation 188, in which the image process device 112 identifies the image as an image showing a fundus. As such, the image is considered to include the fundus to be detected, and thus treated as being near or in fundus. Then, the image process device 112 can perform subsequent operations, such as the operation 160 in FIG. 5.

FIG. 7 schematically illustrates different images with different average color values and edge characteristics. In the illustrated example, a fundus 192 is shown in different sizes in different images 190. The fundus 192 can be identified by an edge or contour 194 and have a color 196. By way of example, the size of the fundus 192 is bigger in a second image 190B than in a first image 190A. In a third image 190C, the apparatus 102 has moved into the fundus 192. In a fourth image 190D, the apparatus 102 has further moved into the fundus 192. As such, the size of the fundus in an image can change the average color value and the edge characteristic of the image. Based on this relationship, the average color value and/or the edge characteristic of an image can be used to determine whether the image includes a fundus.

Figure 8:
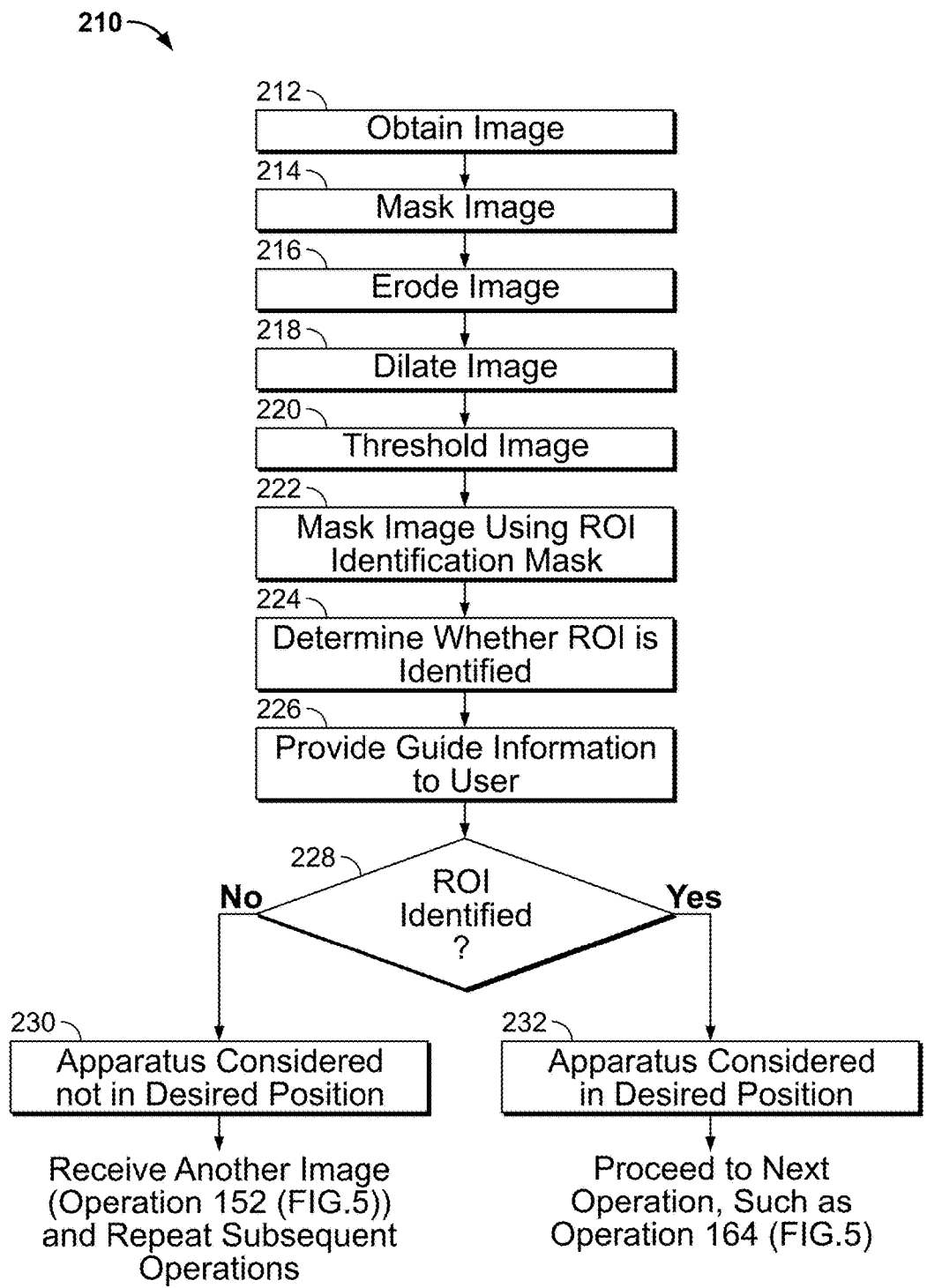
FIG. 8 is a flowchart of an example method for identifying a region of interest in an image.

FIG. 8 is a flowchart of an example method 210 for identifying a region of interest (ROI) in the image. In some examples, the method 210 is performed by the image process device 112 to implement the operation 158 in FIG. 5. In the method 210, the image process device 112 locates a ROI in the image. Once the image has been identified as showing a fundus in the method 170 (FIG. 6), the image is further processed and evaluated to locate a ROI in the image. In some examples, the ROI is the center of the fundus in the image. In other examples, another location in the image can be identified as the ROI.

In one implementation, the steps in the method 210 are implemented as a software application running on a computing device, as illustrated in FIG. 21. In some embodiments, the method 210 is developed with OpenCV library. Other libraries can also be used to implement the steps of the method 210.

Although the method 210 is described to include the operations illustrated in FIG. 8, it is also possible in other examples that the method 210 includes only some of these operations, and/or additional operations associated with the operations described herein. For example, some of the illustrated operations are optional depending on the attributes (e.g., size or quality) of the captured image.

At operation 212, the image process device 112 obtains an image. In some examples, the image is the originally-sized image that corresponds with the scaled image processed in the method 170 as described in FIG. 6.

At operation 214, the image process device 112 applies a mask to the image to remove any non-fundus area. Various known masks can be used for this purpose.

At operation 216, the image process device 112 erodes the image to remove noises, such as irrelevant or minor features in the image. At operation 218, the image process device 112 dilates the image. At operation 220, the image process device 112 thresholds the image to further segment the image and remove all pixels that are too dark or too bright. The thresholding process is used to separate out regions of the image corresponding to the fundus to be analyzed. For example, a binary threshold (e.g., a threshold to zero function in OpenCV) can be used to perform thresholding in this operation. The thresholding process can separate regions in the image based on the variation of intensity between the pixels corresponding to the region of interest and the pixels of background.

At operation 222, the image process device 112 applies an ROI identification mask 300 (such as in FIG. 10) to the image. The ROI identification mask is configured to distinguish one or more things that are not typically regions of interest but end up in certain areas consistently. Such things include facial portions or elements around or adjacent the eye or fundus, such as eyelid, nose, eyebrow, and forehead. When a glare is found in an image, which resembles the reflection from a region of interest in the eye, it may be in fact the reflection off of other regions that are not in interest, such as outside the eye or fundus. As described herein, the ROI identification mask operates to identify the region of interest, distinguishing it from regions that are not in interest.

In some examples, the ROI identification mask is configured to break up contours in regions of the image that may cause false positive errors. As described herein, the ROI identification mask is configured to break one or more contours in the image into pieces. The image process device can then measure the area of each piece, identify the piece with the largest area as a ROI, and then calculate the centroid of the ROI. The centroid of the ROI is mapped to the actual image (or identified in the actual image) and used as a target point, which can be presented in the display device of the apparatus 102. An example of the ROI identification mask 300 is illustrated in more detail with reference to FIG. 10.

At operation 224, the image process device 112 determines whether the ROI is identified in the image. As described above, once the ROI identification mask is applied, the image process device can measure the area of each piece, identify the piece with the largest area as a ROI, and then calculate the centroid of the ROI to use it as the target point. In some examples, the ROI is considered to be identified when the target point is positioned at a predetermined location in the image or on the display screen of the apparatus 102. An example of this operation is illustrated in more detail with reference to FIG. 9.

At operation 226, the image process device 112 generates and provides guide information to the user of the apparatus 102. In some examples, the guide information is presented via the display device 114 of the apparatus 102. An example of the guide information is illustrated with reference to FIGS. 11-15.

At operation 228, if it is determined that the ROI has not been identified ("NO" at this operation), the method 210 moves on to operation 230, in which the image process device 112 recognizes that the apparatus 102 is not arranged in a desired position to capture a fundus image. Then, the image process device 112 can receive another image taken by the image capture device 110 (at the operation 152) and perform the subsequent operations as described herein.

Alternatively, if it is determined that the ROI has been identified ("YES" at this operation), the method 210 goes to operation 232, in which the image process device 112 considers that the apparatus 102 is in a desired position to capture a fundus image. As such, it is regarded that the image includes the fundus and that the ROI has been identified. Then, the image process device 112 can perform subsequent operations, such as the operation 164 in FIG. 5.

Figure 9:
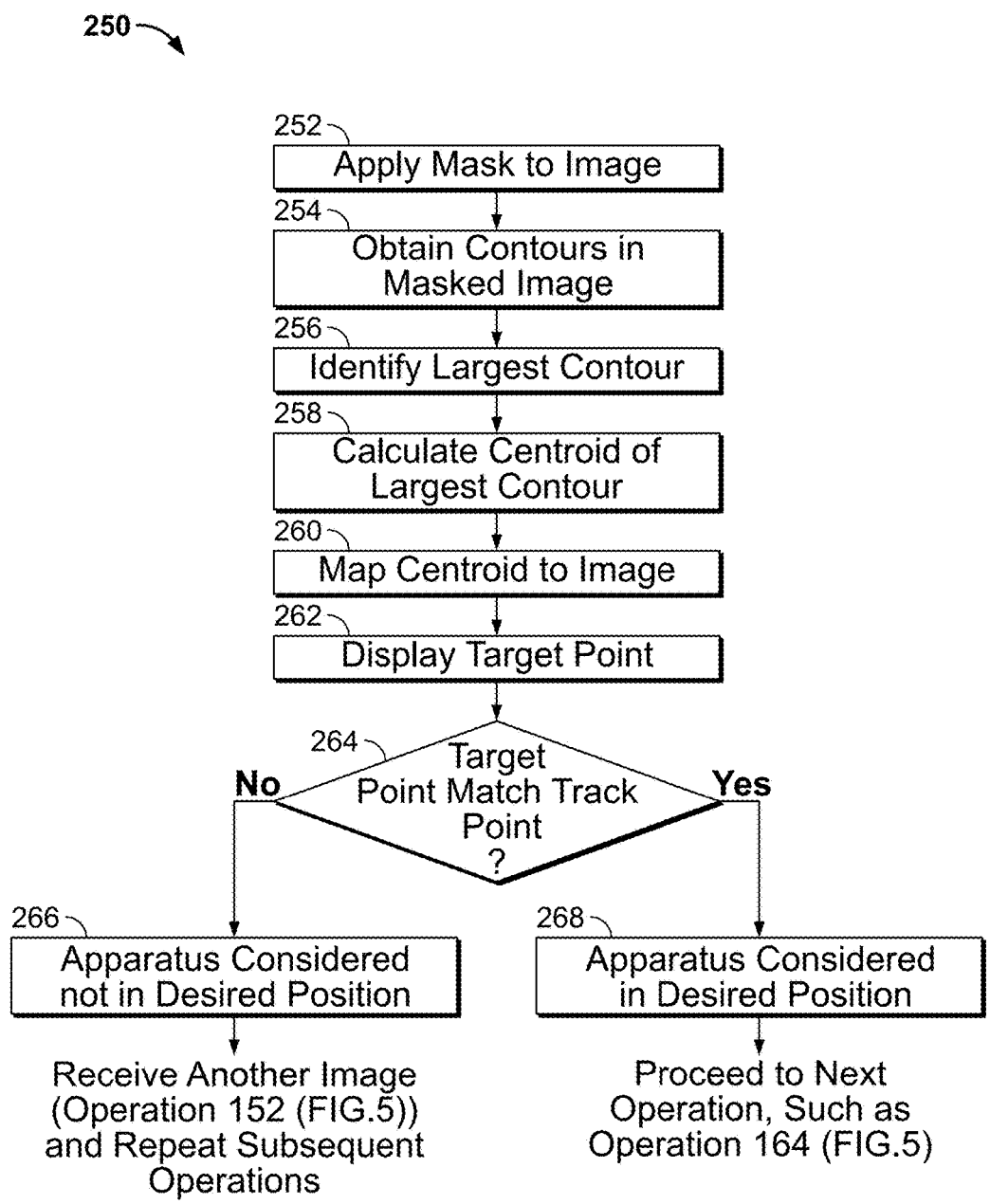
FIG. 9 is a flowchart of an example method for guiding a user to track a region of interest in the image as the user operates the fundus image capture apparatus.
Figure 10:
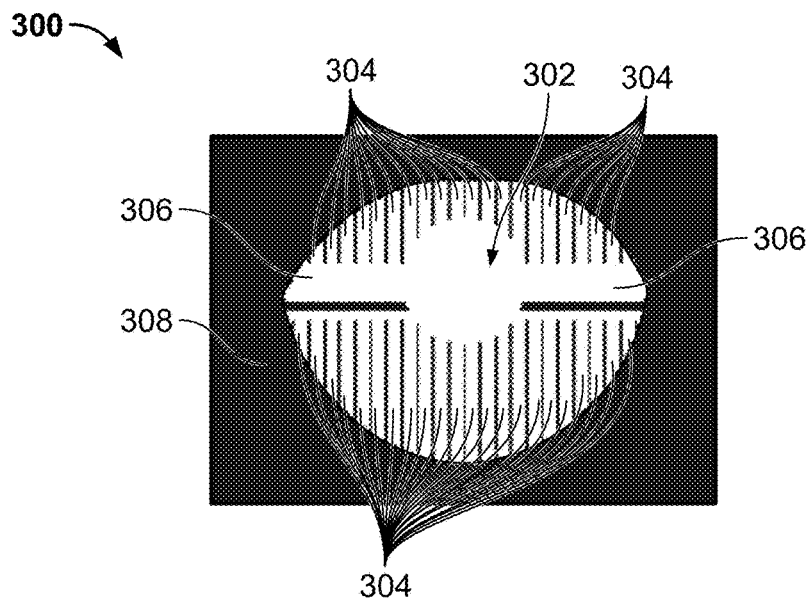
FIG. 10 illustrates an example ROI identification mask.

FIG. 9 is a flowchart of an example method 250 for guiding a user to track a region of interest (ROI) in the image as the user operates the fundus image capture apparatus 102. The method 250 is described with also reference to FIGS. 10-15. FIG. 10 illustrates an example ROI identification mask to be applied to track the ROI in the image. FIGS. 11-15 illustrate five example images captured and displayed in the display device, and five example diagrams that demonstrate image processing to track the ROI in the image.

As described herein, in some examples, the region of interest is a predetermined location of the fundus, such as the center of the fundus in the image. In some examples, the method 250 is performed by one or more devices in the apparatus 102 to implement at least one of the operations 222, 224, 226, 228, 230, and 232 in the method 210, as described in FIG. 8. Although the method 250 is primarily described below to be executed by the image process device 112, it is noted that other devices of the apparatus 102, such as the display device 114, the position measure device 116, and the target guide device 118, can also be used to perform at least part of the method 250.

In one implementation, the steps in the method 250 are implemented as a software application running on a computing device, as illustrated in FIG. 21. In some embodiments, the method 250 is developed with OpenCV library. Other libraries can also be used to implement the steps of the method 250.

Although the method 250 is described to include the operations illustrated in FIG. 9, it is also possible in other examples that the method 250 includes only some of these operations, and/or additional operations associated with the operations described herein. For example, some of the illustrated operations are optional depending on the attributes (e.g., size or quality) of the captured image.

The method 250 can begin at operation 252, in which a mask is applied to the image. In some examples, the mask can be an ROI identification mask 300, as illustrated in FIG. 10. The ROI identification mask 300 operates to distinguish things that are not typically regions of interest, and identify an ROI.

As illustrated in FIG. 10, the ROI identification mask 300 is configured to filter the image into one or more segments or pieces. For example, the ROI identification mask 300 breaks up contours in the image into segments or pieces. By way of example, in FIGS. 11-15, when the ROI identification mask 300 is applied to the image 330, a diagram 332 that represents data about the masked image demonstrates a plurality of segments 350, which are also referred to herein as masked contours 350, or simply as blobs or contours 350. In the masked image or diagram 332, the contours 350 are defined as enclosed, contiguous areas.

In some examples, the ROI identification mask 300 is configured to be in the same size as images 330 captured and displayed in the apparatus 102. The same ROI identification mask 300 is applied to different images 330 captured as the apparatus 102 moves against the subject's face or eye.

In some examples, the ROI identification mask 300 defines a center filter region and wedge-shaped filter regions arranged around the center filter regions. This configuration ensures that the reflection shown in the image is from the eye, not from something else.

For example, the ROI identification mask 300 defines a center region 302 that selectively filters a corresponding region of the captured image 330. In addition, the ROI identification mask 300 includes a plurality of longitudinal regions 304 that selectively filter corresponding regions of the captured image 330. In some examples, the longitudinal regions 304 are connected to, and extend from, the center region 302. In some examples, the longitudinal regions 304 extend in parallel and are spaced apart from each other with predetermined gaps. In the illustrated example, the longitudinal regions 304 extend vertically. In other examples, the longitudinal regions 304 can extend in different directions.

In addition, the ROI identification mask 300 includes a crossing region 306 configured to selectively filter a corresponding region of the captured image 330. The crossing region 306 can run across the mask 300. In some examples, the crossing region 306 extends through the center region 302. The crossing region 306 is arranged to modify and distribute the masking area as desired. In the illustrated example, the crossing region 306 runs horizontally. In other examples, the crossing region 306 can extend in different directions.

With the crossing region 306, the longitudinal regions 304 are separated into two groups, one group of longitudinal regions (e.g., at the upper side of the mask) being spaced apart from the other group of longitudinal regions (e.g., at the lower side of the mask). With the configuration of the center region 302, the longitudinal regions 304 and the crossing region 306, the target point (or the centroid of the largest contour) can be moved smoothly. For example, when the user moves the apparatus 102, the target point 370 appears to move smoothly on the display screen.

The regions of the mask 300, such as the center region 302, the longitudinal regions 304, and the crossing region 306, are defined by a surrounding portion 308 configured to block corresponding regions of the image to which the mask is applied.

In some examples, the center region 302, the longitudinal regions 304, and the crossing region 306 are configured to filter the corresponding regions of the image 330 to which the mask 300 is applied, when the pixels of the corresponding regions have predetermined values. Where the image 330 is a grayscale image, the regions 302, 304, and 306 of the mask 300 filter the pixels having values greater than a threshold value. The other portions of the mask 300, such as the surrounding portion 308, block all pixels of corresponding portions of the image.

As exemplified in FIGS. 11-15, the center region 302 of the mask 300 is arranged at a location in which a desired object or element (i.e., the region of interest) is supposed to be arranged in the image. In contrast, the longitudinal regions 304 of the mask 300 are arranged at a location in which objects or elements that are not in interest (i.e., false positive errors) are typically arranged.

Figure 11:
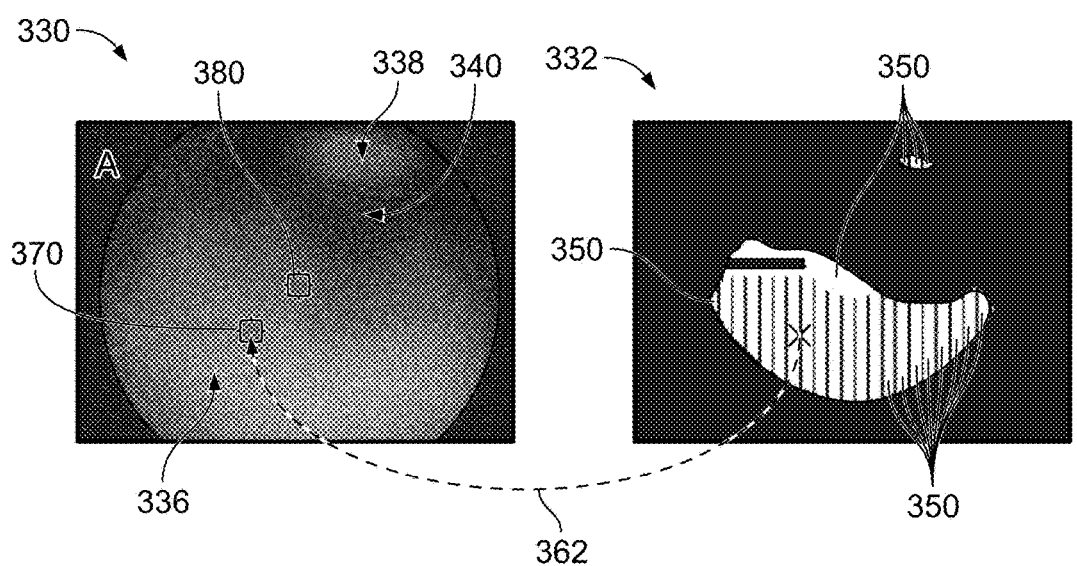
FIG. 11 illustrates an example image and a corresponding masked image.

For example, in FIG. 11, the image 330 generally captures regions outside the pupil and does not show the region of interest, such as the center of fundus. In fact, a contour of reflection 336 at a lower side of the image 330 shows the eyelid and part of the eyeball. A contour of reflection 338 at an upper side of the image 330 is actually part of the pupil, and a dark region 340 is the rest of the pupil. As such, the contours 336, 338, and 340 are generally not regions of interest, and are positioned primarily over the longitudinal regions 304 in the mask 300. As shown in the masked image 332, the contours 336, 338, and 340 are generally filtered by the longitudinal regions 304 of the mask 300, resulting in multiple small pieces of masked contours 350 in the masked image 332.

Figure 15:
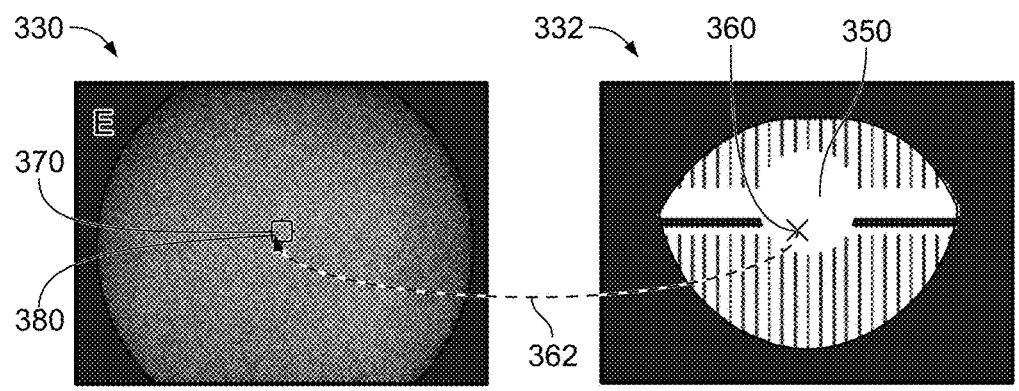
FIG. 15 illustrates yet another example image and a corresponding masked image.

In contrast, as shown in FIG. 15, the image 330 captures inside of the fundus and shows the region of interest. As shown, the region of interest (e.g., the center of fundus) is positioned over the center region 302 in the mask 300. Thus, the region of interest is filtered primarily by the center region 302 of the mask 300, resulting in a single large contour 350 in the masked image 332.

Referring again to FIG. 9, once the image 330 is masked (operation 252), the image process device 112 obtains contours 350 in the masked image 332, at operation 254. As illustrated in FIGS. 11-15, the contours 350 are defined as enclosed, contiguous regions in the masked image 332, and are separated from each other. In the illustrated example, the contours 350 in the masked image 332 are formed by the center region 302, the longitudinal regions 304, and/or the crossing region 306 of the mask 300 when the mask 300 is applied to the image 330.

At operation 256, the image process device 112 identifies the largest contour 350. In some examples, the image process device 112 calculates the area of each contour 350 in the masked image 332, and compares between the areas of the contours 350 to determine one of the contours 350 that has the largest area. In some examples, the area is calculated by the number of pixels within each contour. In other examples, the areas are determined by relative sizes of the contours. Other methods can be used to calculate the area of each contour in other examples.

At operation 258, the image process device 112 calculates a centroid 360 of the largest contour 350. The centroid 360 indicates a center of mass of the largest contour. In some examples, the largest contour is assumed to be of uniform density. Such a centroid can be determined in various methods.

Figure 12:
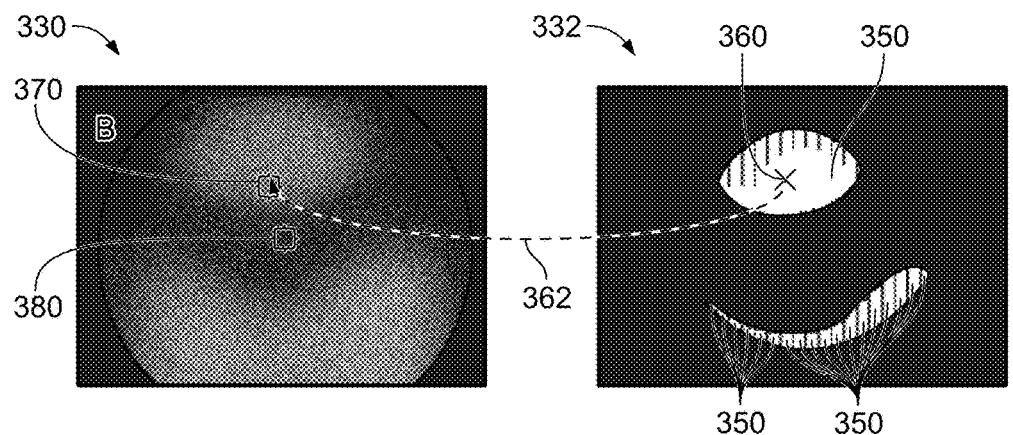
FIG. 12 illustrates another example image and a corresponding masked image.
Figure 13:
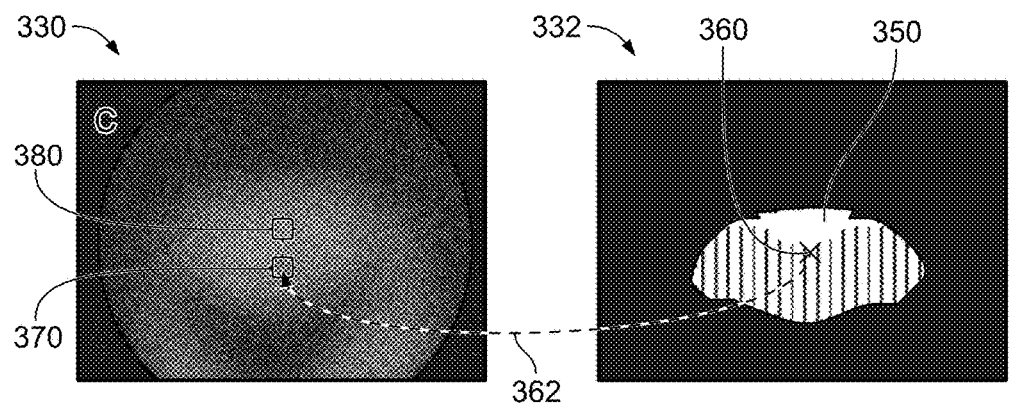
FIG. 13 illustrates yet another example image and a corresponding masked image.
Figure 14:
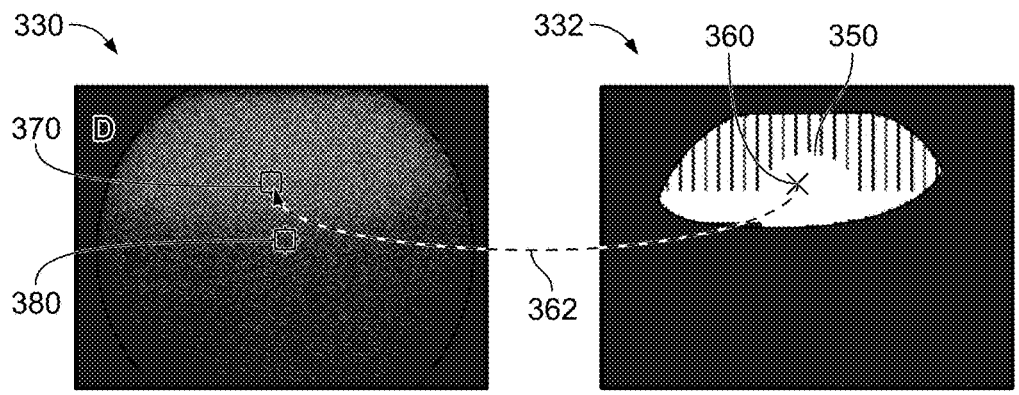
FIG. 14 illustrates yet another example image and a corresponding masked image.

By way of example, in FIG. 12, the masked image 332 includes a single contour 350 at the upper side and twenty (20) contours 350 at the lower side of the masked image 332. The image process device 112 would determine the upper-side contour 350 as the largest contour in the masked image and calculate the centroid 360 of the upper-side contour 350. The centroid 360 in the other masked images 332 (FIGS. 10 and 13-15) is similarly obtained.

At operation 260, the image process device 112 maps the centroid 360 of the largest contour 350 to the image 330. The mapping 362 of the centroid 360 is illustrated in FIGS. 11-15.

At operation 262, the image process device 112 generates and displays a target point 370 on the display screen of the apparatus 102. As illustrated, the target point 370 is placed over the image 330 shown in the display screen. The target point 370 is presented at a location to which the centroid 360 is mapped. Therefore, the target point 370 can represent the centroid of the largest contour, which can correspond to the center of the region of interest. The target point 370 is used as a guide mark that assists the user to move the apparatus 102 until the ROI is identified (as illustrated in FIG. 15). As illustrated in FIGS. 11-15, the target point 370 moves on the display screen as the apparatus 102 moves by the user's operation against the subject's face or eye.

At operation 264, the image process device 112 determines whether the target point 370 matches a track point 380 on the display screen of the apparatus 102.

Along with the target point 370, the track point 380 is used to guide the user to move the apparatus 102 to desired position and orientation to capture a desired image. In some examples, the track point 380 is arranged and fixed at a predetermined location of the field of view (and thus the display screen). For example, the track point 380 is arranged at the center of the field of view (i.e., at the center of the display screen). The mask 300 can be applied to each image 330 such that the center of the center region 302 in the mask 300 is aligned to correspond to the track point 380 in the image 330.

The track point 380 functions as a reference point to which the target point 370 needs to fit. As the apparatus 102 moves, the target point 370 can move because the images captured by the apparatus 102 are different depending on the position of the apparatus 102 against the subject. However, the track point 380 is fixed on the display screen of the apparatus 102, and represents a point to which the apparatus 102 should be arranged and oriented. Therefore, the user is required to move the apparatus 102 until the target point 370 matches the target point 380. As such, the target point 370 and the track point 380 are configured to assist the user move, arrange, and orient the apparatus 102 without paying attention to what the user are actually looking at through the display device. The user only needs to keep moving the target point 370 into the track point 380.

In the illustrated example, the target point 370 is presented as a solid ball or square, and the track point 380 is displayed as a hollow circle or square. Other shapes or characteristics of the target point 370 and the track point 380 are possible in other examples.

By way of example, in FIGS. 11-14, the target point 370 does not match the track point 380, which indicates that the apparatus 102 is not arranged against the subject's eye as desired to identify the ROI, such as the center of fundus. In contrast, in FIG. 15, the target point 370 matches the track point 380, thereby representing that the apparatus 102 is appropriately arranged and oriented against the subject's eye, and that the captured image 330 includes and identifies the ROI as desired.

In some examples, to improve readability, the colors of the target point 370 and/or the track point 380 can change depending on the position of the target point 370 relative to the track point 380. In one embodiment, the target point 370 and the track point 380 has a first color (e.g., red) when the target point 370 and the track point 380 are misaligned as in FIGS. 11-14, and change their color to a second color (e.g., green) when the target point 370 is overlapped with the track point 380 as shown in FIG. 15. Other color schemes are also possible. In other examples, in addition or alternatively to the color scheme, various visual and/or tactile schemes can be used to indicate the matching between the target point 370 and the track point 380. For example, when the target point 370 and the track point 380 are aligned, the points 370 and 380 can blink, and/or provide tactile feedback (e.g., vibration or haptic effect) to the user through the apparatus.

Referring still to FIG. 9, at operation 264, if it is determined that the target point 370 does not match the track point 380 ("NO" at this operation), the method 250 moves on to operation 266, in which the image process device 112 recognizes that the apparatus 102 is not arranged in a desired position to capture a fundus image. Then, the image process device 112 can receive another image taken by the image capture device 110 (at the operation 152 in FIG. 5) and perform the subsequent operations as described herein.

Alternatively, if it is determined that the target point 370 matches the track point 380 ("YES" at this operation), the method 250 goes to operation 268, in which the image process device 112 considers that the apparatus 102 is in a desired position to capture a fundus image. As such, it is regarded that the image includes the fundus and that the ROI has been identified. Then, the image process device 112 can perform subsequent operations, such as the operation 164 in FIG. 5.

Referring to FIGS. 11-15, the method 250 is further described, which is to guide the user until the user moves the apparatus 102 to a desired position against the subject. In FIGS. 11-15, the images 330 illustrate example images displayed on the display screen such that the user can monitor the images being captured by the apparatus 102 while moving the apparatus 102 against the subject. The masked images 332 are example results of applying the ROI identification mask 300 to the corresponding images 330, respectively.

In FIGS. 11-14, when the image 330 is filtered with the ROI identification mask 300, one or more contours 350 (e.g., multiple contours in FIGS. 11 and 12, and one contour in FIGS. 13 and 14) are generated as illustrated in the masked image 332. Then, the largest contour 350 is identified and the centroid 360 is calculated. The centroid 360 is then mapped into the image 330, and the mapped location is represented by the target point 370 in the image 330. As shown, the target point 370 is not fit into the track point 380 that is fixed in the center of the display screen (and thus the center of the image 330). Thus, the user needs to move the apparatus 102 to try to match the target point 370 with the track point 380.

As such, the ROI identification mask 300 is used to identify the region of interest. Without the ROI identification mask 300, for example, the image 330 in FIG. 12 may be interpreted such that the region of interest is in the lower region of the image when, in fact, the lower region in the image is the subject's lower eyelid.

In FIG. 15, when the image 330 is filtered with the ROI identification mask 300, one contour 350 is generated as illustrated in the masked image 332. Then, the centroid 360 of the contour 350 is calculated. The centroid 360 is then mapped into the image 330, and the mapped location is represented by the target point 370 in the image 330. As shown, the target point 370 matches the track point 380. Thus, the apparatus 102 is appropriately arranged against the subject's fundus, and the image 330 contains the fundus and the desired ROI.

Figure 16:
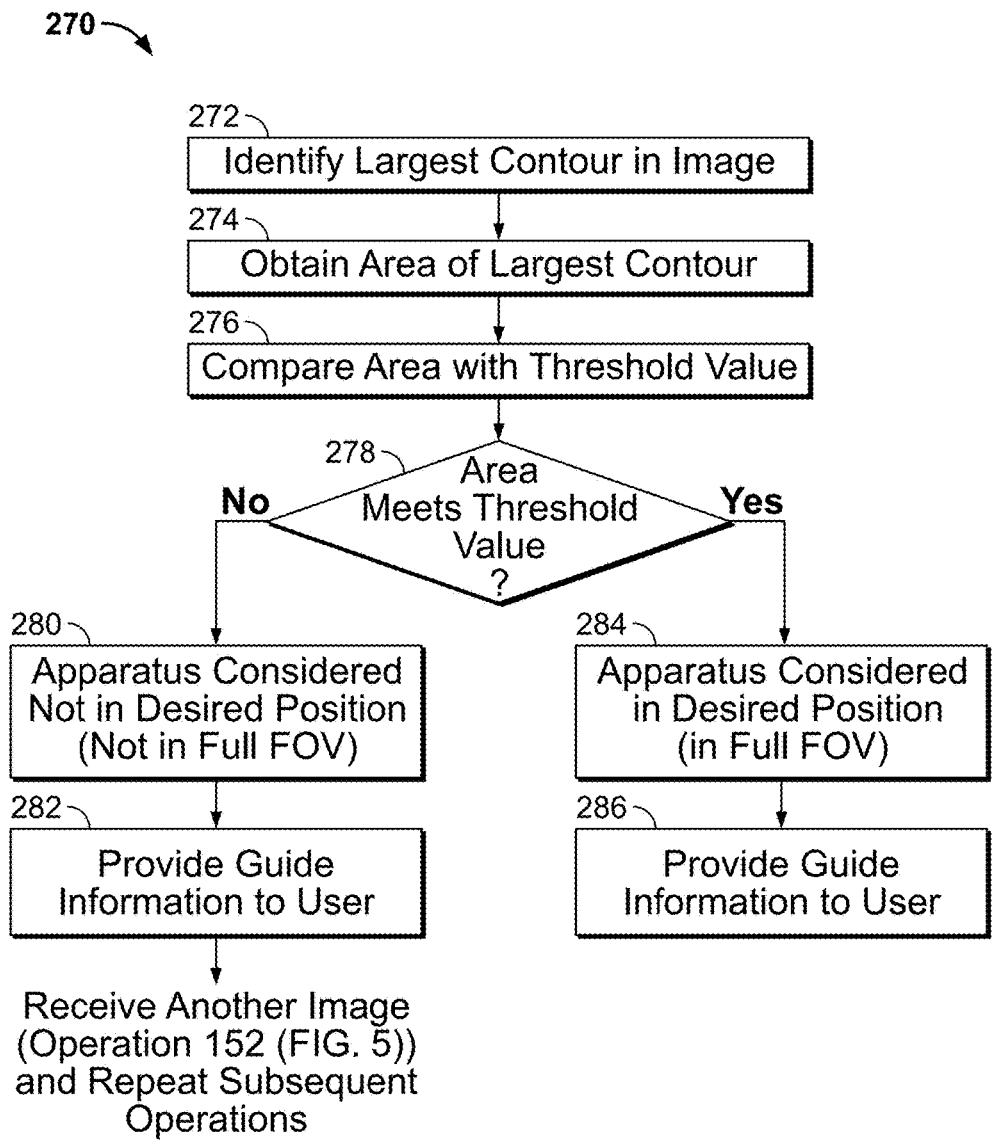
FIG. 16 is a flowchart of an example method for determining a field of view of the image.
Figure 17:
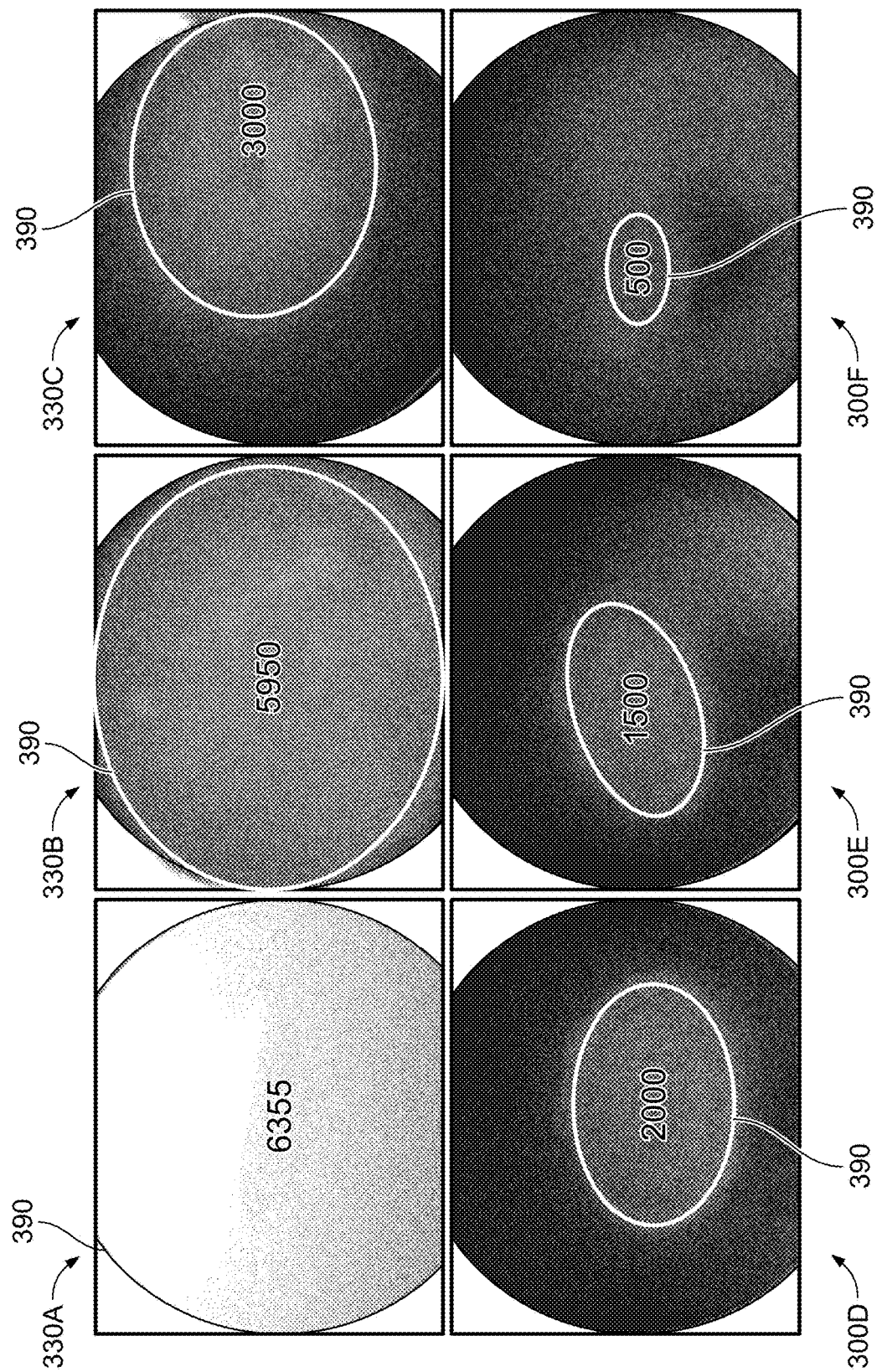
FIG. 17 shows example images with different fields of view.
Figure 18:
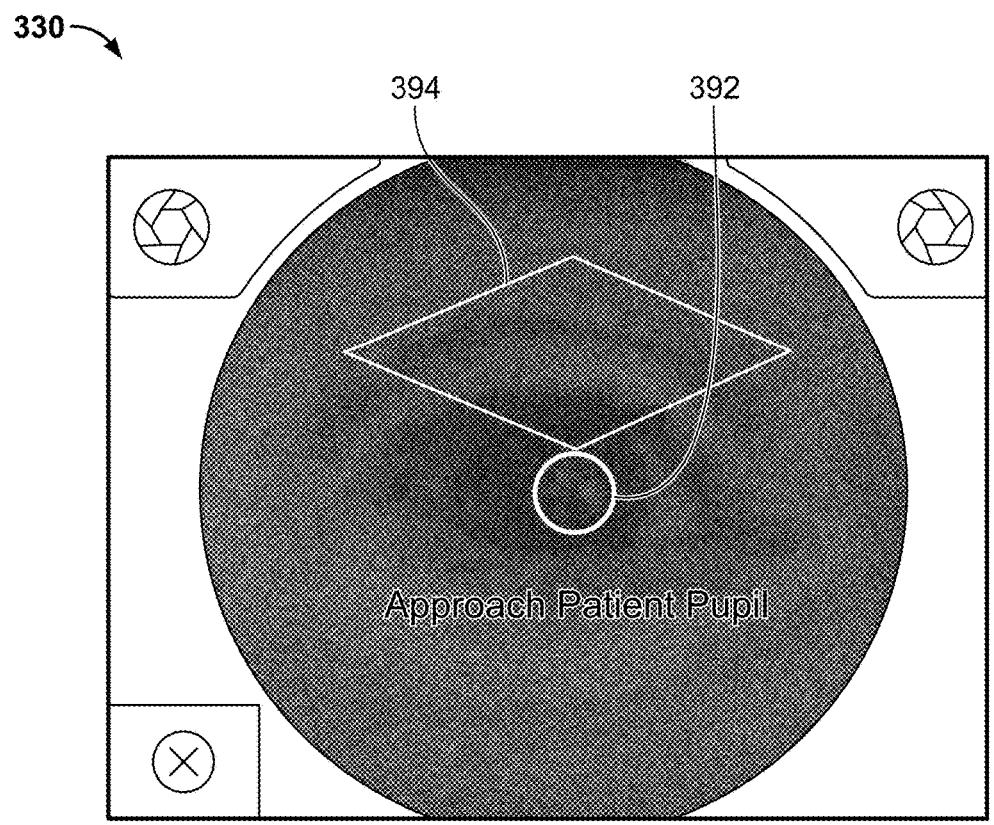
FIG. 18 illustrates an example image displayed with a field of view.
Figure 19:
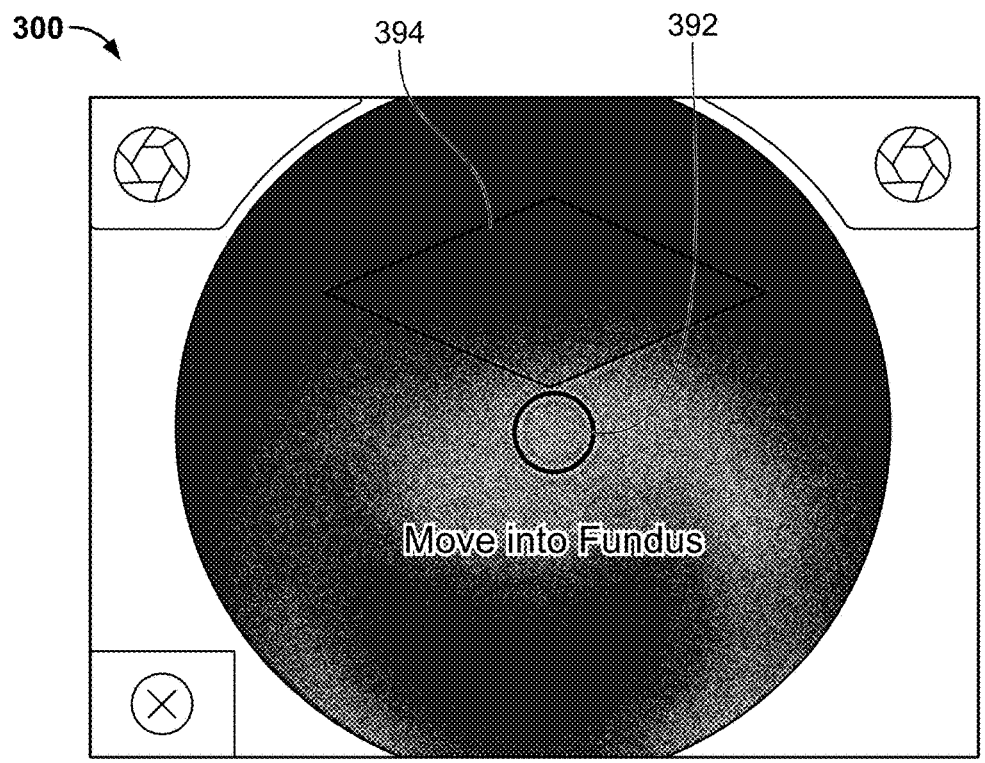
FIG. 19 illustrates another example image displayed with another field of view.
Figure 20:
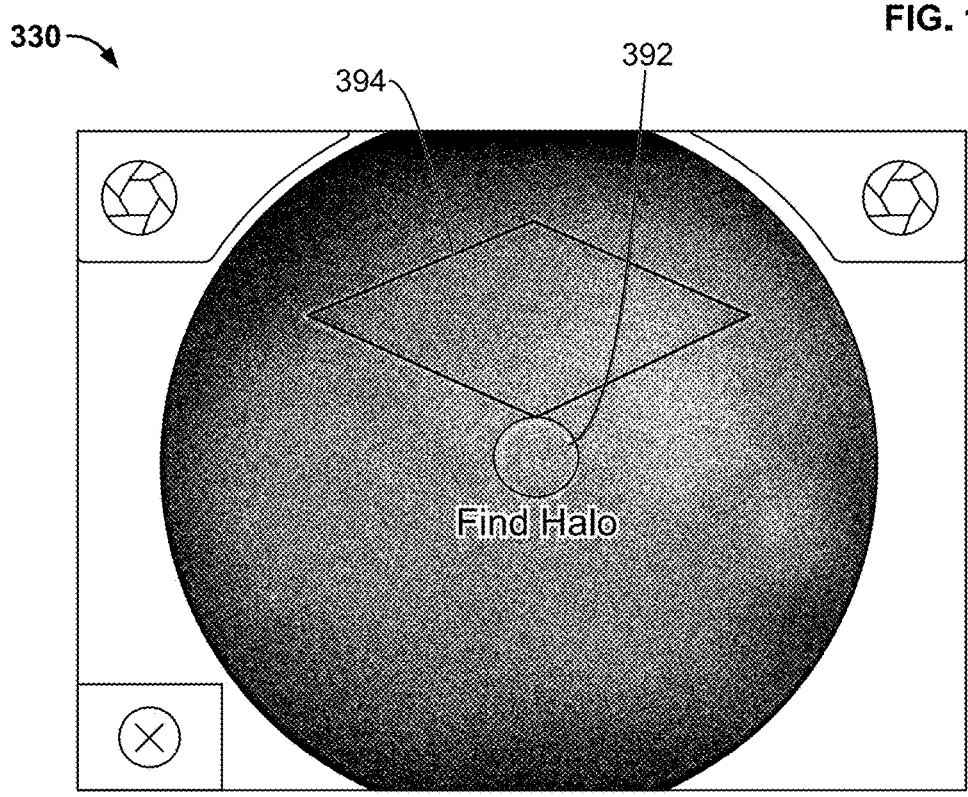
FIG. 20 illustrates yet another example image displayed with yet another field of view.

FIG. 16 is a flowchart of an example method 270 for determining a field of view (FOV) of the image. The method 270 further allows the user to move the apparatus 102 to achieve a desired field of view. The method 270 is described with also reference to FIGS. 17-20. FIG. 17 shows example images with different fields of view. FIGS. 18-20 illustrate three example images displayed in the display device while the field of view is adjusted.

In some examples, the method 270 is performed by one or more devices in the apparatus 102 to implement the operation 164 in FIG. 5. Although the method 270 is primarily described below to be executed by the image process device 112, it is noted that other devices of the apparatus 102, such as the display device 114, the position measure device 116, and the target guide device 118, can also be used to perform at least part of the method 270.

In one implementation, the steps in the method 270 are implemented as a software application running on a computing device, as illustrated in FIG. 21. In some embodiments, the method 270 is developed with OpenCV library. Other libraries can also be used to implement the steps of the method 270.

Although the method 270 is described to include the operations illustrated in FIG. 16, it is also possible in other examples that the method 270 includes only some of these operations, and/or additional operations associated with the operations described herein. For example, some of the illustrated operations are optional depending on the attributes (e.g., size or quality) of the captured image.

Once the apparatus 102 is arranged to view the inside of the fundus, the apparatus 102 can further operate to ensure that the apparatus 102 is arranged appropriately to capture the fundus in a full field of view. As the field of view from the apparatus 102 comes into the area of the fundus, the apparatus 102 further operates to assist the user to adjust the position and/or orientation of the apparatus to make the best field of view. The method 270 helps the user achieve the full field of view while the apparatus 102 is not in a desired position or orientation due to the user's improper operation of the apparatus and/or the subject's sudden movement.

The method 270 begins at operation 272, in which the image process device 112 identifies a largest contour 390 (FIG. 17) in the image 330. As illustrated in FIG. 17, different images 330 (such as 330A-F) have different largest contours 390.

In some examples, the largest contour 390 can be identified by processing and evaluating the image 330, independently from the other operations described herein. In other examples, the largest contour 390 can be identified from one or more of the operations described herein, such as the operations 252, 254, and 256 in the method 250 (FIG. 9). In yet other examples, the largest contour 390 can be obtained in operations that are separate from the other operations described herein but perform similarly to one or more of the other operations.

At operation 274, the image process device 112 obtains the area of the largest contour 390. The area of the largest contour 390 can be used to represent the current field of view of the image, which reveals the user's current depth into the fundus.

In some examples, the area is calculated by the number of pixels within the contour 390. In other examples, the area is determined by a relative size of the contour 390. Other methods can be used to calculate the area of the largest contour 390 in other examples.

At operation 276, the image process device 112 compares the area of the largest contour 390 with a threshold value. The threshold value is representative of a desired field of view in the image. In some examples, the threshold value is a single predetermined value. In other examples, the threshold value is a range of value.

At operation 278, the image process device 112 determines whether the area of the largest contour 390 meets the threshold value. Where the threshold value is a range of value, the area can be considered to meet the threshold value if the area falls within the range of value.

By way of example, if the area (e.g., the number of pixels) of the largest contour 390 is less than a first value (e.g., 1000 pixels), it is considered that the threshold value is not met, and the image is regarded as not having a desired field of view. For example, the image 330F has the largest contour 390 having an area smaller than the first value. This can imply that the image captures completely outside of the fundus.

If the area of the largest contour 390 ranges between the first value (e.g., 1000 pixels) and a second value (e.g., 2500 pixels), it is considered that the threshold value is still not met, and the image is regarded as not having a desired field of view. However, it can imply that the field of view from the apparatus is partially moving into the fundus. For example, the images 330D and 330E have the largest contours 390 having areas between the first and second values, and thus represent that the field of view has partially entered into the fundus.

If the area of the largest contour 390 ranges between the second value (e.g., 2500 pixels) and a third value (e.g., 6000 pixels), it is considered that the threshold value is met, and the image is regarded as having a desired field of view. Thus, it implies that the field of view from the apparatus has completely moved into the fundus. For example, the images 330B and 330C have the largest contours 390 having areas between the second and third values, and thus represent that the field of view has entered into the fundus. In some examples, the apparatus may still need to slightly adjust its angle to reach the full field of view.

If the area of the largest contour 390 is greater than the third value (e.g., 6000 pixels), it is considered that the threshold is not met, and the image is regarded as not having a desired field of view. This may indicate a false positive error, which implies that the apparatus is completely outside the fundus. For example, the image 330A has the largest contour 390 with the area greater than the third value. However, the image 330A is actually an image of the subject's cheek when the apparatus 102 is pressed against it.

Referring still to FIG. 17, if it is determined that the area of the largest contour 390 does not meet the threshold ("NO" at this operation), the method 270 moves on to operation 280, in which the image process device 112 recognizes that the apparatus 102 is not arranged in a desired position to capture a fundus image (e.g., not in a desired field of view). Then, at operation 282, the image process device 112 (and/or the display device 114 and the target guide device 118) provides guide information to the user to assist the user to move the apparatus 102 until the apparatus 102 reaches to its desired position (with the desired field of view). The image process device 112 can further receive another image taken by the image capture device 110 (at the operation 152 in FIG. 5) and perform the subsequent operations as described herein.

Alternatively, if it is determined that the area of the largest contour 390 meets the threshold ("YES" at this operation), the method 270 goes to operation 284, in which the image process device 112 considers that the apparatus 102 is in a desired position (e.g., with a desired field of view) to capture a fundus image. As such, it is regarded that the image includes the fundus and that the full field of view has been achieved. Then, the image process device 112 can provide guide information to the user to inform that the apparatus 102 is in place (operation 286).

Referring to FIGS. 18-20, a method is described for providing guide information when the user moves the apparatus 102 relative to the subject. In FIGS. 18-20, the images 330 illustrate example images displayed on the display screen such that the user can monitor the images being captured by the apparatus 102 while moving the apparatus 102 against the subject. The information displayed on the screen can assist the user to move the apparatus to a desired position and orientation.

In FIGS. 18 and 19, when the user locates the apparatus 102 completely out of fundus (FIG. 18) or in fundus without a full field of view (FIG. 19), a first mark 392 is activated, and a second mark 394 is deactivated. The first mark 392 can be designed in various ways. In the illustrated example, the first mark 392 is configured as a circle in the center of the display screen. The first mark 392 can be activated or deactivated in various ways. In some example, the first mark 392 changes its color when activated. For example, the first mark 392 remains in gray color or dimmed when deactivated, and changes to green when activated. Other color schemes or designs are also possible in other examples.

In FIG. 20, when the user locates the apparatus 102 into fundus with a relatively full field of view, the second mark 394 is activated, and the first mark 392 is deactivated. The second mark 394 can be designed in various ways. In the illustrated example, the second mark 394 is configured as a diamond shape arranged at an upper side of the display screen. The second mark 394 can be activated or deactivated in various ways. In some examples, the second mark 394 changes its color when activated. For example, the second mark 394 remains in gray color or dimmed when deactivated, and changes to green when activated. Other color schemes or designs are also possible in other examples.

FIG. 21 illustrates an exemplary architecture of a computing device 400 which can be used to implement aspects of the present disclosure, including the fundus image capture system 102 (or the image capture device 110, the image process device 112, the display device 114, the position measure device 116, and/or the target guide device 118, separately), the server computing device 104, and the network 106, and will be referred to herein as the computing device 400. The computing device 400 is used to execute the operating system, application programs, and software modules (including the software engines) described herein.

The computing device 400 can be of various types. In some embodiments, the computing device 400 is a desktop computer, a laptop computer, or other devices configured to process digital instructions. In other embodiments, the computing device 400 is a mobile computing device. Examples of the computing device 400 as a mobile computing device include a mobile device (e.g., a smart phone and a tablet computer), a wearable computer (e.g., a smartwatch and a head-mounted display), a personal digital assistant (PDA), a handheld game console, a portable media player, a ultra-mobile PC, a digital still camera, a digital video camera, and other mobile devices.

The computing device 400 includes, in some embodiments, at least one processing device 402, such as a central processing unit (CPU). A variety of processing devices are available from a variety of manufacturers, for example, Intel or Advanced Micro Devices. In this example, the computing device 400 also includes a system memory 404, and a system bus 406 that couples various system components including the system memory 404 to the processing device 402. The system bus 406 is one of any number of types of bus structures including a memory bus, or memory controller; a peripheral bus; and a local bus using any of a variety of bus architectures.

The system memory 404 includes read only memory 408 and random access memory 410. A basic input/output system 412 containing the basic routines that act to transfer information within the computing device 400, such as during start up, is typically stored in the read only memory 408.

The computing device 400 also includes a secondary storage device 414 in some embodiments, such as a hard disk drive, for storing digital data. The secondary storage device 414 is connected to the system bus 406 by a secondary storage interface 416. The secondary storage devices and their associated computer readable media provide nonvolatile storage of computer readable instructions (including application programs and program modules), data structures, and other data for the computing device 400.

Although the exemplary environment described herein employs a hard disk drive as a secondary storage device, other types of computer readable storage media are used in other embodiments. Examples of these other types of computer readable storage media include magnetic cassettes, flash memory cards, digital video disks, Bernoulli cartridges, compact disc read only memories, digital versatile disk read only memories, random access memories, or read only memories. Some embodiments include non-transitory media.

A number of program modules can be stored in secondary storage device 414 or memory 404, including an operating system 418, one or more application programs 420, other program modules 422, and program data 424.

In some embodiments, the computing device 400 includes input devices to enable a user to provide inputs to the computing device 400. Examples of input devices 426 include a keyboard 428, a pointer input device 430, a microphone 432, and a touch sensitive display 440. Other embodiments include other input devices. The input devices are often connected to the processing device 402 through an input/output interface 438 that is coupled to the system bus 406. These input devices 426 can be connected by any number of input/output interfaces, such as a parallel port, serial port, game port, or a universal serial bus. Wireless communication between input devices and interface 438 is possible as well, and includes infrared, BLUETOOTH® wireless technology, 802.11a/b/g/n, cellular, or other radio frequency communication systems in some possible embodiments.

In this example embodiment, a touch sensitive display device 440 is also connected to the system bus 406 via an interface, such as a video adapter 442. The touch sensitive display device 440 includes touch sensors for receiving input from a user when the user touches the display. Such sensors can be capacitive sensors, pressure sensors, or other touch sensors. The sensors not only detect contact with the display, but also the location of the contact and movement of the contact over time. For example, a user can move a finger or stylus across the screen to provide written inputs. The written inputs are evaluated and, in some embodiments, converted into text inputs.

In addition to the display device 440, the computing device 400 can include various other peripheral devices (not shown), such as speakers or a printer.

The computing device 400 further includes a communication device 446 configured to establish communication across the network. In some embodiments, when used in a local area networking environment or a wide area networking environment (such as the Internet), the computing device 400 is typically connected to the network through a network interface, such as a wireless network interface 450. Other possible embodiments use other wired and/or wireless communication devices. For example, some embodiments of the computing device 400 include an Ethernet network interface, or a modem for communicating across the network. In yet other embodiments, the communication device 446 is capable of short-range wireless communication. Short-range wireless communication is one-way or two-way short-range to medium-range wireless communication. Short-range wireless communication can be established according to various technologies and protocols. Examples of short-range wireless communication include a radio frequency identification (RFID), a near field communication (NFC), a Bluetooth technology, and a Wi-Fi technology.

The computing device 400 typically includes at least some form of computer-readable media. Computer readable media includes any available media that can be accessed by the computing device 400. By way of example, computer-readable media include computer readable storage media and computer readable communication media.

Computer readable storage media includes volatile and nonvolatile, removable and non-removable media implemented in any device configured to store information such as computer readable instructions, data structures, program modules or other data. Computer readable storage media includes, but is not limited to, random access memory, read only memory, electrically erasable programmable read only memory, flash memory or other memory technology, compact disc read only memory, digital versatile disks or other optical storage, magnetic cassettes, magnetic tape, magnetic disk storage or other magnetic storage devices, or any other medium that can be used to store the desired information and that can be accessed by the computing device 400. Computer readable storage media does not include computer readable communication media.

Computer readable communication media typically embodies computer readable instructions, data structures, program modules or other data in a modulated data signal such as a carrier wave or other transport mechanism and includes any information delivery media. The term "modulated data signal" refers to a signal that has one or more of its characteristics set or changed in such a manner as to encode information in the signal. By way of example, computer readable communication media includes wired media such as a wired network or direct-wired connection, and wireless media such as acoustic, radio frequency, infrared, and other wireless media. Combinations of any of the above are also included within the scope of computer readable media.

The computing device illustrated in FIG. 21 is also an example of programmable electronics, which may include one or more such computing devices, and when multiple computing devices are included, such computing devices can be coupled together with a suitable data communication network so as to collectively perform the various functions, methods, or operations disclosed herein.

Referring again to FIG. 21, the computing device 400 can include a location identification device 448. The location identification device 448 is configured to identify the location or geolocation of the computing device 400. The location identification device 448 can use various types of geolocating or positioning systems, such as network-based systems, handset-based systems, SIM-based systems, Wi-Fi positioning systems, and hybrid positioning systems. Network-based systems utilize service provider's network infrastructure, such as cell tower triangulation. Handset-based systems typically use the Global Positioning System (GPS). Wi-Fi positioning systems can be used when GPS is inadequate due to various causes including multipath and signal blockage indoors. Hybrid positioning systems use a combination of network-based and handset-based technologies for location determination, such as Assisted GPS.

As such, the fundus image capture system of the present disclosure provides values that can be used to define if the user has found the reflection (e.g., IR reflection) from the pupil, the centroid (i.e., target position) of the region of interest, and the current field of view. This information can be used to guide the user through the fundus capturing process, thereby improving ease of use of the system. The methods implemented in the system of the present disclosure are simple and require less resource, thereby enabling fast image processing and evaluation.

The various examples and teachings described above are provided by way of illustration only and should not be construed to limit the scope of the present disclosure. Those skilled in the art will readily recognize various modifications and changes that may be made without following the examples and applications illustrated and described herein, and without departing from the true spirit and scope of the present disclosure.

What is claimed is:

1. An apparatus for producing a fundus image, the apparatus comprising:
   a processor;
   an image capture device for capturing images; and
   a non-transitory computer readable storage device storing software instructions that, when executed by the processor, cause the apparatus to:
      obtain an image from the image capture device;
      apply a mask to the image to generate a masked image;
      identify a predetermined contour in the masked image, the predetermined contour being at least a portion of the masked image;
      calculate a centroid of the predetermined contour; and
      generate guide information, prior to capture of an image, usable to guide a user to operate the apparatus to capture the image showing a region of interest, the guide information generated based on the centroid of the predetermined contour, and the guide information including:
         a target point on the display device, the target point being arranged at a location corresponding to the centroid of the predetermined contour in the masked image; and
         a track point on the display device, the track point being fixed at a center of a field of view of the display to function as a reference for positioning of the target point.

2. The apparatus of claim 1, wherein the region of interest is a predetermined location of an eye fundus.

3. The apparatus of claim 1, wherein the non-transitory computer readable storage device stores further software instructions that, when executed by the processor, cause the apparatus device to:
   determine whether the region of interest is identified in the image.

4. The apparatus of claim 1, wherein the mask is configured to selectively filter the image into one or more contours in the masked image, the contours being defined as enclosed, contiguous filtered areas in the masked image.

5. The apparatus of claim 4, wherein the predetermined contour is a largest contour in the masked image.

6. The apparatus of claim 5, wherein the mask defines a center region and a plurality of longitudinal regions, the center region and the longitudinal regions configured to selectively filter corresponding regions of the image, the longitudinal regions extending from the center region and being spaced apart from each other with predetermined gaps.

7. The apparatus of claim 6, wherein the mask further defines a crossing region configured to selectively filter a corresponding region of the image and running across the center region.

8. The apparatus of claim 1, wherein the mask is applied to the image such that the center region corresponds to the track point.

9. The apparatus of claim 8, wherein the non-transitory computer readable storage device stores further software instructions that, when executed by the processor, cause the apparatus device to:
   determine that the region of interest is identified in the image upon the target point matching the track point.

10. The apparatus of claim 1, wherein the non-transitory computer readable storage device stores further software instructions that, when executed by the processor, cause the apparatus device to:
    determine whether the image has a predetermined characteristic representative of an eye fundus.

11. The apparatus of claim 10, wherein the predetermined characteristic is associated with at least one of an average color value and an edge characteristic.

12. The apparatus of claim 10, wherein the non-transitory computer readable storage device stores further software instructions that, when executed by the processor, cause the apparatus device to:
    prior to determining, resize the image to a smaller size.

13. A method of capturing an eye fundus image, the method comprising:

obtaining an image from an image capture device;

applying a mask to the image to generate a masked image;

identifying, by a computing device, a largest contour in the masked image, the largest contour being at least a portion of the masked image;

calculating a centroid of the largest contour;

displaying the image on a display device; and displaying a target point on the display device, the target point being arranged at a location in the image corresponding to the centroid of the largest contour in the masked image.

14. The method of claim 13, further comprising:

displaying a track point on the display device.

15. The method of claim 14, wherein the track point is arranged at a fixed location relative to the display device while the target point is changeable in location in different images.

16. The method of claim 15, further comprising:

determining that a region of interest is identified in the image upon the target point matching the track point.

* * * * *